United States Patent
Wolfinbarger, Jr. et al.

(10) Patent No.: US 8,574,826 B2
(45) Date of Patent: *Nov. 5, 2013

(54) PROCESS FOR DECELLULARIZING SOFT-TISSUE ENGINEERED MEDICAL IMPLANTS, AND DECELLULARIZED SOFT-TISSUE MEDICAL IMPLANTS PRODUCED

(75) Inventors: Lloyd Wolfinbarger, Jr., Norfolk, VA (US); Perry Lange, Virginia Beach, VA (US); Alyce Linthurst Jones, Virginia Beach, VA (US); Eric Moore, Carrollton, VA (US); Barry Nolf, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/901,135

(22) Filed: Oct. 8, 2010

(65) Prior Publication Data

US 2011/0143438 A1 Jun. 16, 2011

Related U.S. Application Data

(60) Continuation of application No. 12/041,435, filed on Mar. 3, 2008, now abandoned, which is a continuation of application No. 10/624,534, filed on Jul. 23, 2003, now Pat. No. 7,338,757, which is a division of application No. 09/528,371, filed on Mar. 17, 2000, now Pat. No. 6,734,018, which is a continuation-in-part of application No. 09/327,240, filed on Jun. 7, 1999, now abandoned.

(51) Int. Cl.
*A01N 1/00* (2006.01)
*C12N 5/00* (2006.01)

(52) U.S. Cl.
USPC .......................................... 435/1.1; 435/378

(58) Field of Classification Search
None
See application file for complete search history.

(56) References Cited

U.S. PATENT DOCUMENTS

| | | | |
|---|---|---|---|
| 4,776,853 A | 10/1988 | Klement et al. | |
| 4,810,299 A | 3/1989 | Schilling et al. | |
| 5,095,925 A | 3/1992 | Elledge et al. | |
| 5,336,616 A | 8/1994 | Livesey et al. | |
| 5,357,636 A | 10/1994 | Dresdner, Jr. et al. | |
| 5,432,712 A | 7/1995 | Chan | |
| 5,531,791 A | 7/1996 | Wolfinbarger, Jr. | |
| 5,556,379 A | 9/1996 | Wolfinbarger | |
| 5,558,875 A | 9/1996 | Wang | |
| 5,613,982 A | 3/1997 | Goldstein | |
| 5,632,778 A | 5/1997 | Goldstein | |
| 5,820,581 A | 10/1998 | Wolfinbarger, Jr. | |
| 5,843,180 A | 12/1998 | Jaffe et al. | |
| 5,843,181 A | 12/1998 | Jaffee et al. | |
| 5,843,182 A | 12/1998 | Goldstein | |
| 5,855,620 A | 1/1999 | Bishopric et al. | |
| 5,863,531 A | 1/1999 | Naughton et al. | |
| 5,885,617 A | 3/1999 | Jordan | |
| 5,899,936 A | 5/1999 | Goldstein | |
| 5,916,266 A | 6/1999 | Yui et al. | |
| 5,976,104 A | 11/1999 | Wolfinbarger, Jr. | |
| 5,993,844 A | 11/1999 | Abraham et al. | |
| 5,997,896 A | 12/1999 | Carr, Jr. et al. | |
| 6,024,735 A | 2/2000 | Wolfinbarger, Jr. | |
| 6,293,970 B1 | 9/2001 | Wolfinbarger, Jr. | |
| 6,312,474 B1 | 11/2001 | Francis et al. | |
| 6,371,992 B1 | 4/2002 | Tanagho et al. | |
| 6,376,244 B1 | 4/2002 | Atala | |
| 6,416,995 B1 | 7/2002 | Wolfinbarger, Jr. | |
| 6,428,802 B1 | 8/2002 | Atala | |
| 6,432,710 B1 | 8/2002 | Boss, Jr. et al. | |
| 6,448,076 B2 | 9/2002 | Dennis et al. | |
| 6,479,064 B1 | 11/2002 | Atala | |
| 2001/0049138 A1 | 12/2001 | Dennis et al. | |

OTHER PUBLICATIONS

Clark et al. (2003) Decellularized dermal grafting in cleft palate repair, Facial Plastic Surg., 5:40-44.

Conklin et al. (2002) Development and evaluation of a novel decellularized vascular xenograft, Medical Engineering and Physics, 24:173-183.

Courtman et al. (1992) The acellular matrix vascular prosthesis: investigation of its potential as a xenograpft for clinical application, Biomaterial Tissue Interfaces, 10:241-246.

Courtman et al. (1994) Development of a pericardial acellular matrix biomaterial: biochemical and mechanical effects of a cell extraction, J. Biomedical Materials Research, 28:655-666.

Courtman et al. (1995) Biomechanical and ultrastructural comparison of cryopreservation and a novel cellular extraction of porcine aortic valve leaflets, J. Biomedical Materials Research, 29:1507-1516.

(Continued)

*Primary Examiner* — Sandra Saucier
(74) *Attorney, Agent, or Firm* — Morgan, Lewis & Bockius LLP

(57) ABSTRACT

The invention provides methodologies and apparatus for producing a cellular soft-tissue implants, both in small quantities and in commercializable quantities. Such soft-tissue implants include vascular graft substitutes. An acellular graft is produced by subjecting the tissue sample to an induced pressure mediated flow of an extracting solution, followed by inducing a pressure mediated flow of a treating solution, then washing the treated tissue to produce the acellular graft. The acellular grafts produced are uniform and nonimmunogenic.

The inventive method allows for the production of multiple decellularized soft tissue implants, where processing time is significantly less than prior art processes and the number of implants produced per day is increased over prior art processes. In clinical use, the decellularized grafts produced exhibit significantly improved in long-term durability and function.

18 Claims, 18 Drawing Sheets

(56) References Cited

OTHER PUBLICATIONS

Dohmen et al. (2002) In vitro hydrodynamics of a decellularized pulmonary porcine valve, compared with a glutaridehyde and polyurethane heart valve, J. Artifical Organs, 25(11):1089-1094.

Dohmen et al. (2002) Ross operation with a tissue-engineered heart valve, Society of Thoracic Surgeons, pp. 1438-1442.

Elkins et al. (2001) Decellularized human valve allografts, Society of Thoracic Surgeons, pp. S428-S432.

Goldstein et al. (2000) Transpecies heart valve transplant: advanced studies of a bioengineered xeno-autograft, Society of Thoracic Surgeons, pp. 1963-1969.

Korrossis et al. (2002) Tissue engineering of cardiac valve prosthesis II: biomechanical characterization of decellularized porcine aortic heart valves, Heart Valve Disease, 11(4):463-471.

Madden et al. (2002) Decellularized cadaver vein allografts used for hemodialysis access do not cause allosensitization or preclude kidney transplantation, J. Kidney Diseases, 40(6):1240-1243.

Moreno et al. (1991) Contribution to the study of the enzymatic activity of benzonase, J. Molecular Catalysis, 69(3):419-427.

Sievers et al. (2003) Decellularized pulmonary homograft (SynerGraft) for reconstruction of the right ventricular outflow tract: first clinical experince, Z. Karkiol., 92:53.

Wilson et al. (1990) Acellular matrix allograpft small caliber vascular prosthesis, Trans. Am. Sog. Artif. Intern. Organs, vol. 36:M340-M343.

Wilson et al. (1995) Acellular matrix: a biomaterials approach for coronary artery bypass and heart valve replacement, Society of Thoracic Surgeons, pp. S353-S358.

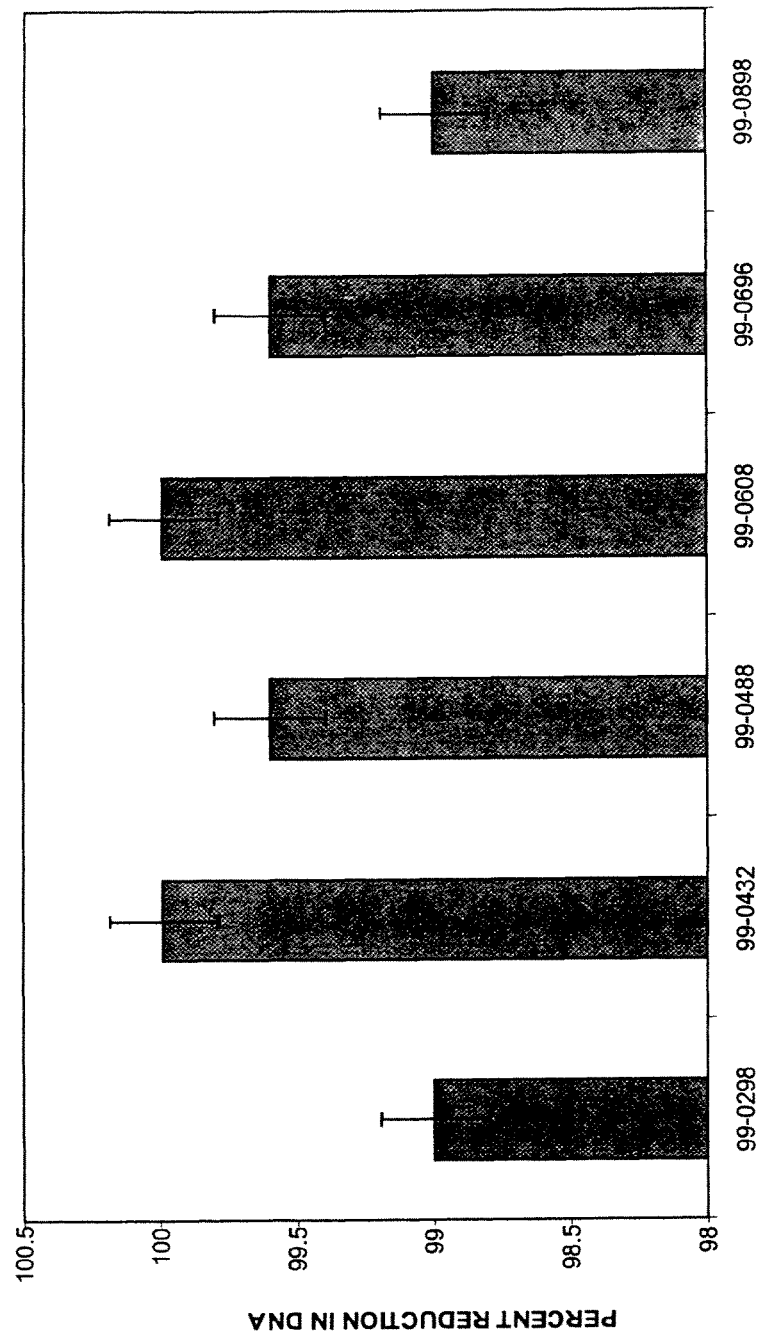

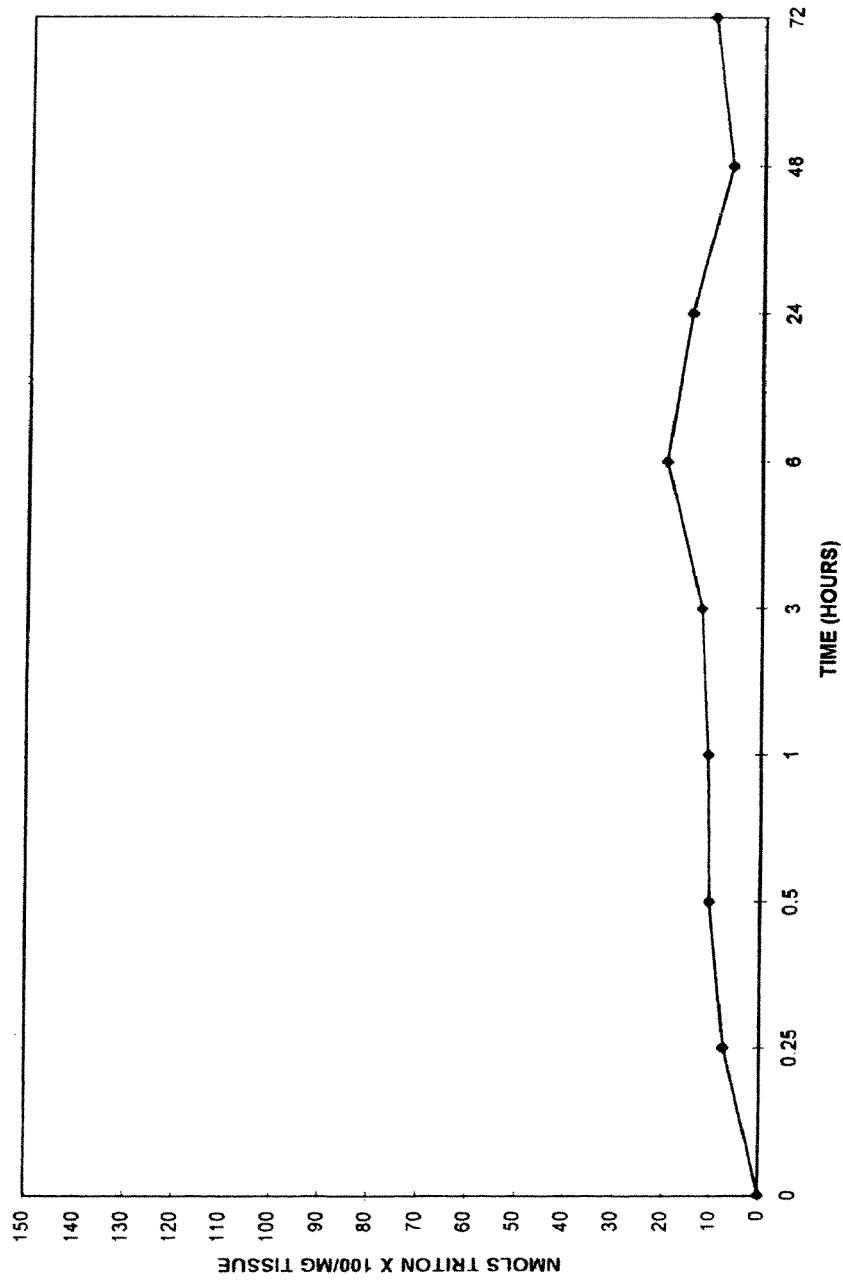

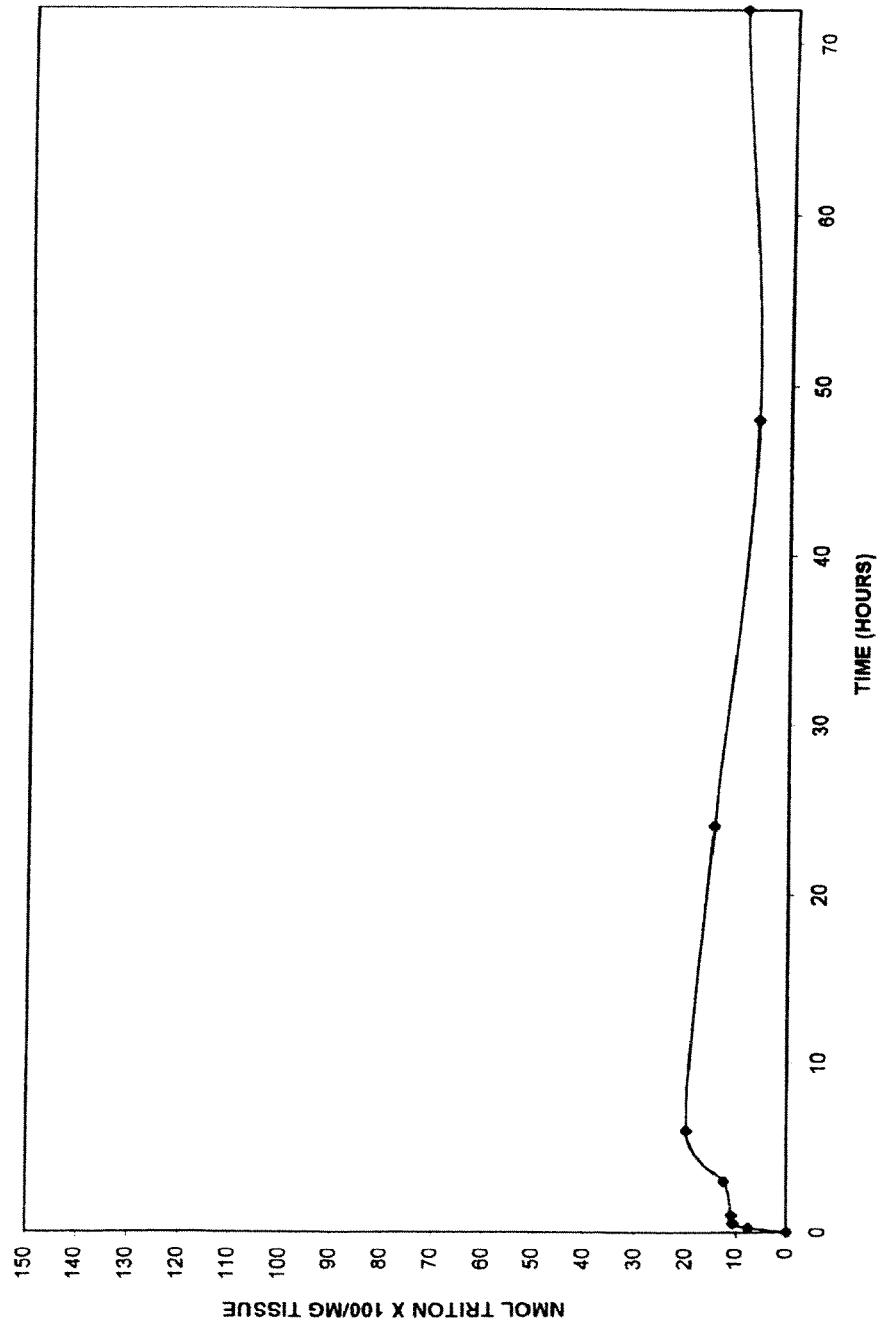

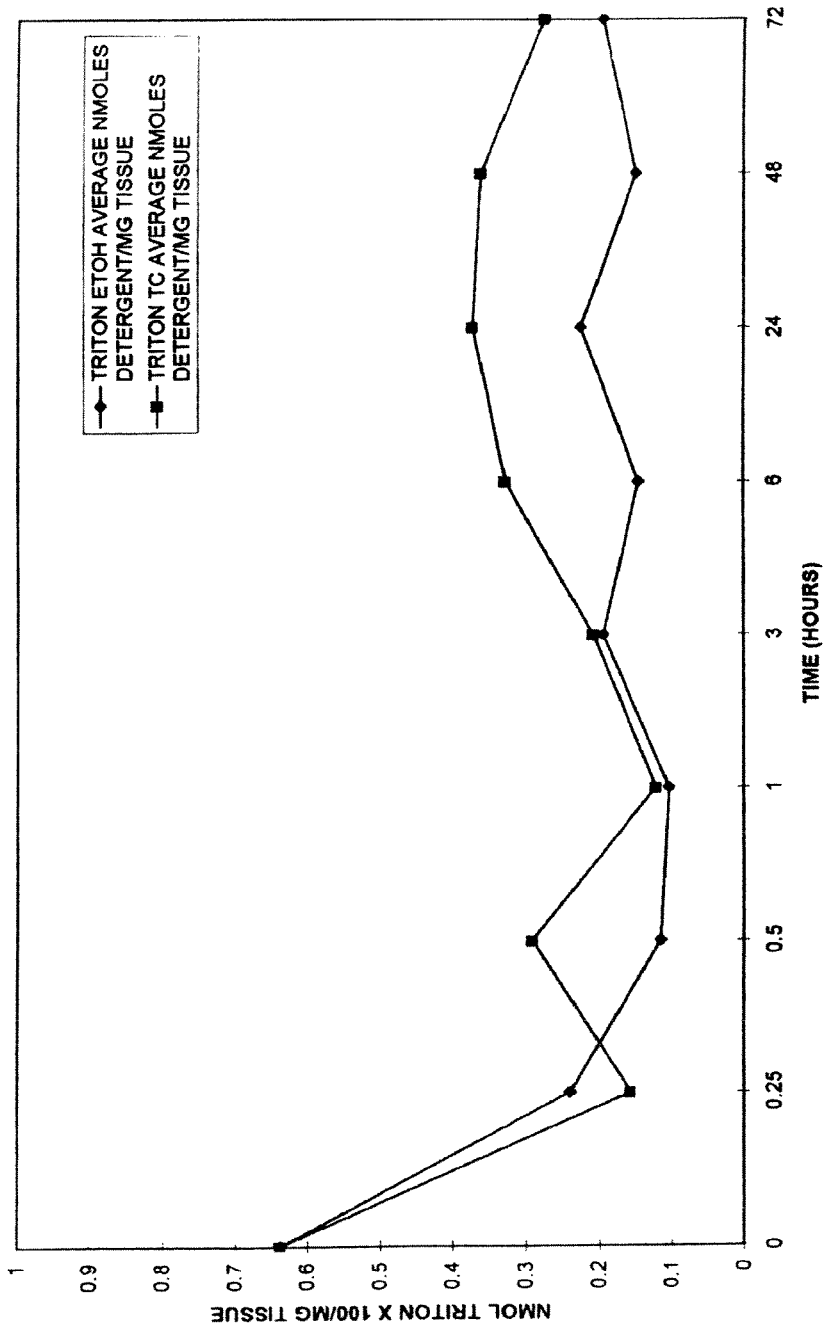

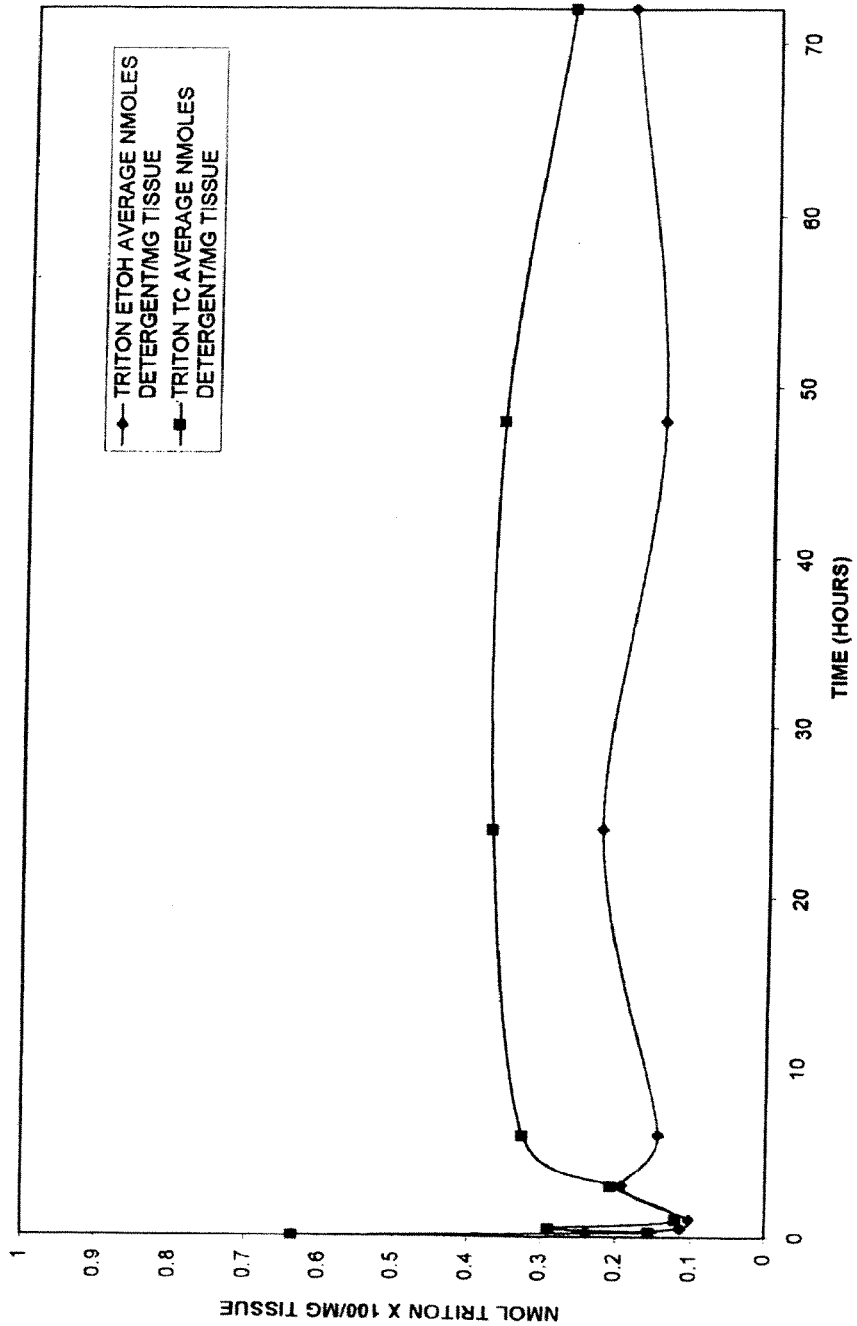

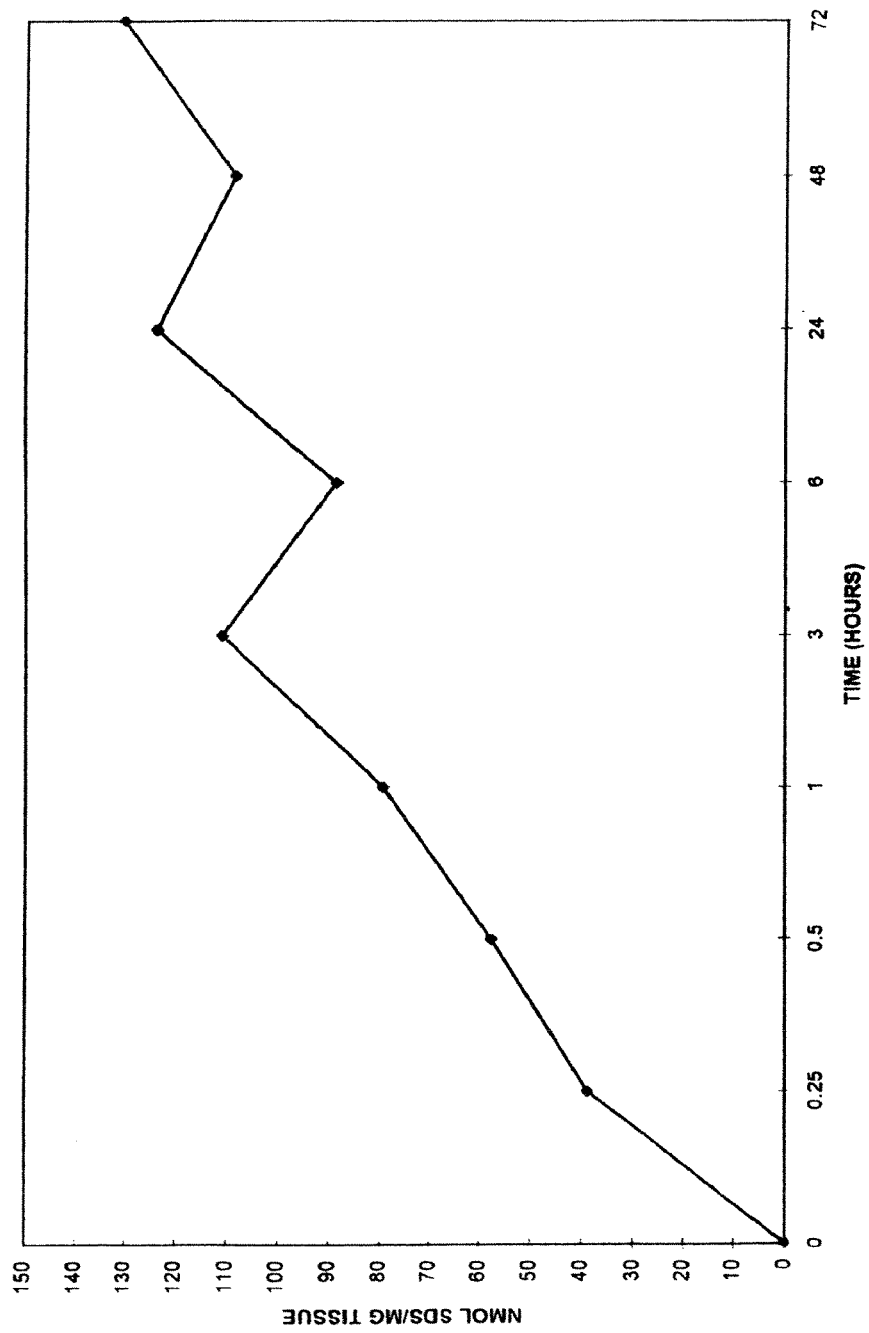

KINETICS FOR 3H SDS BINDING TO SAPHENOUS VEIN TISSUE
(92-0515)

AMOUNT OF 3H SDS REMAINING IN SAPHENOUS VEIN TISSUE EXTRACTED WITH 70% ETHANOL OR TISSUE CULTURE MEDIA
(98-0730)

AMOUNT OF 3H SDS BOUND TO SAPHENOUS VEIN EXTRACTED IN 70% ETHANOL OR TISSUE CULTURE MEDIA (98-0730)

PROCESS FOR DECELLULARIZING SOFT-TISSUE ENGINEERED MEDICAL IMPLANTS, AND DECELLULARIZED SOFT-TISSUE MEDICAL IMPLANTS PRODUCED

This is a continuation application of U.S. application Ser. No. 12/041,435, filed Mar. 3, 2008 now abandoned, which is a continuation of U.S. application Ser. No. 10/624,534, filed Jul. 23, 2003, now U.S. Pat. No. 7,338,757, which is a divisional application of U.S. application Ser. No. 09/528,371, filed Mar. 17, 2000, now U.S. Pat. No. 6,734,018, which is a continuation-in-part application of U.S. application Ser. No. 09/327,240, filed Jun. 7, 1999 now abandoned, all of which are herein incorporated by reference in their entireties.

FIELD OF THE INVENTION

The invention is directed toward methodologies and apparatus for use in the preparation of acellular, i.e. essentially lacking in living cells andi or non-living cells, soft-tissue implants, in small quantities and commercializable quantities. Such soft-tissue implants include vascular graft substitutes. These implants can be derived from tissue engineered soft tissue devices, tissue products derived from animal or human donors that contain or are devoid of cells, and that contain or are devoid of valve structures useful in directing the flow of fluids through tubular vascular devices, and/or combinations of natural tissue products and tissue engineered soft-tissue products. The invention includes methodologies and apparatus for producing uniform, gently processed, decellularized multiple soft tissue implants, where processing time is significantly reduced and the number of implants produced per day is increased. The decellularized grafts produced are significantly improved in long-term durability and function when used in clinical applications.

BACKGROUND OF THE INVENTION

Numerous types of vascular graft substitutes have been produced in the last four decades. These vascular graft substitutes have included large and small diameter vascular, blood carrying tubular structures, grafts containing valvular structures (vein substitutes, and heart valve substitutes) and lacking valvular structures (artery substitutes). The materials out of which these vascular grafts have been constructed have included man-made polymers, notably Dacron and Teflon in both knitted and woven configurations, and non-man-made polymers, notably tissue engineered blood vessels such as described in U.S. Pat. Nos. 4,539,716; 4,546,500; 4,835,102; and blood vessels derived from animal or human donors such as described in U.S. Pat. Nos. 4,776,853; 5,558,875; 5,855,617; 5,843,181; and 5,843,180.

The prior art processing methods are prohibitively time consuming, easily requiring numerous days, for example anywhere from eight to twenty-one days total processing time. Such long processing times result in proteolytic degradation of the matrix structures of the processed tissues. Over the past few decades numerous efforts have been made to manage the large surgical use of vascular prostheses in the treatment of vascular dysfunctions/pathologies. While vascular prostheses are available for clinical use, they have met with limited success due to cellular and immunological complications, and the inability to remain patent and function. These problems are especially pronounced for small diameter prostheses, i.e. less than about 6 mm. Efforts have been directed at removing those aspects of allograft and xenograft vascular prostheses that contribute to immunological "rejection" and these efforts have focused primarily on development of various "decellularization" processes, which processes require unduly burdensome incubation times. In addition the prior art methods involve using volumes of processing solutions which do not lend themselves to the production of large numbers of vascular grafts, which ability to "scale-up" is necessary for economic clinical use.

The inventive process produces a cellular grafts including but not limited to ligaments, tendons, menisci, cartilage, skin, pericardium, dura mater, fascia, small and large intestine, placenta, veins, arteries, and heart valves. The process is advantageous over prior art processes in that processing times and conditions have been optimized and reduced, and the economics of production have been dramatically improved, resulting in large numbers of uniform, non-immunogenic grafts being produced. The grafts produced are non-immunogenic, are substantially free from damage to the matrix, and are substantially free from contamination including for example free from infectious agents.

The invention involves the use of an anionic agent, for example sodium dodecylsulfate (SDS), for the treatment of tissues with the dual objective of decellularization and treatment of tissues to restrict recellularization. Further, the invention expands on the process of treating tissue(s) with SDS, describing how the amount(s) of SDS deposited in the tissue(s) can be further enhanced/reduced to either further inhibit recellularization of the tissue OR enhance recellularization of the tissue. Treatment of tissues with salt solutions prior to treatment with SDS results in different patterns of SDS deposition/precipitation in the tissues than treatment of tissues with SDS followed by treatment of tissues with salt solutions. Treatment of tissues with SDS prior to salt treatment can be expected to result in significant binding of SDS, primarily via hydrophobic interactions, to matrix "proteins" with further deposition of SDS in the tissues as salt precipitated materials by salt precipitation post SDS treatment. Treatment of tissues with salt solutions prior to treatment with SDS solutions can be expected to result in significant precipitation of SDS as a salt precipitated form and less SDS being bound to tissue matrix structure(s) via hydrophobic interactions. It is further understood that the particular salt solution used, either prior to or following SDS treatment, can significantly alter the subsequent solubility of the salt precipitated SDS and thus long-term retention of SDS in the tissues post implantation. The observed salt effects on both perceptibility of SDS and subsequent resolubilization of the salt precipitated form of SDS indicate an activity order of Ca>Mg>Mn>K>Na and calcium salts of dodecylsulfate (CaDS) are less soluble and thus more slowly released from treated tissues than, for example, sodium salts of dodecylsulfate (SDS). The invention is directed at a process for producing acellular soft-tissue implants including vascular grafts, veins, arteries, and heart valves, where processing times and conditions have been optimized to dramatically improve on the economics of production as well as to produce a graft with minimum damage to the matrix structure of the acellular graft. It is a further objective of the present invention to describe how to control the amount(s) of anionic detergents, for example sodium dodecylsulfate (SDS), deposited in the tissue(s) with the objective of enhancing or restricting subsequent recellularization.

SUMMARY OF THE INVENTION

The inventive process is a process for preparing biological material(s) for implantation into a mammalian cardiovascular system, musculoskeletal system, or soft tissue system. The process removes cellular membranes, nucleic acids, lipids, and cytoplasmic components and produces an implant having an extracellular matrix including as major components collagens, elastins, proteoglycans, and mucopolysaccharides.

The process provides for the production of commercializable quantities of acellular soft tissue grafts for implantation into mammalian systems by removing the cellular populations, cellular remnants, nucleic acids, and small molecular weight proteins, lipids, and polysaccharides forming an acellular nonsoluble matrix having is major components collagens, elastins, hyaluronins, and proteoglycans. The acellular tissue produced can be implanted into a mammalian system, or recellularized in vitro and subsequently implanted into a mammalian system.

An embodiment of the process includes the following steps:
  isolating from a suitable donor a desired tissue sample of the biological material;
  extracting the tissue with mildly alkaline hypotonic buffered solution of an endonuclease such as Benzonase® (a registered product of Merck KGaA, Darmstadt, Germany) and a nonionic detergent formulation such as Allowash Solution™ (a registered trademark product of LifeNet, Virginia Beach, Va.);
  optionally treating the tissue with a hypertonic buffered salt solution;
  extracting and treating the tissue with a mildly alkaline hypotonic buffered solution of sodium dodecylsulfate, optionally with 0.1 to 0.5 M sodium chloride rendering the solution hypertonic;
  optionally treating the tissue with a hypertonic buffered salt solution;
  washing the tissue with ultrapure water followed by a water solution of chlorine dioxide; and
  storage in a sealed container in isotonic saline, chlorine dioxide or 70% isopropanol.

The invention provides a process for preparing an acellular soft tissue graft for implantation into a mammalian system, including extracting a soft tissue sample with an extracting solution including one or more nonionic detergents and one or more endonucleases, to produce extracted tissue; treating the extracted tissue with a treating solution including one or more anionic detergents, to produce a treated tissue; washing the treated tissue with a decontaminating solution including one or more decontaminating agents to produce the acellular soft tissue graft; and storing the acellular soft tissue graft in a storage solution comprising one or more decontaminating agents.

The invention further provides a process for preparing commercializable quantities of acellular soft tissue grafts for implantation into mammalian systems, including obtaining tissue samples from an acceptable donor; extracting the tissue samples with an extracting solution including one or more nonionic detergents and one or more endonucleases, to produce extracted tissue; treating the extracted tissue with a treating solution including one or more anionic detergents, to produce a treated tissue; washing the treated tissue with a decontaminating solution including one or more decontaminating agents to produce the acellular soft tissue graft; and storing the acellular soft tissue graft in a storage solution including one or more decontaminating agents.

The invention also provides a process for preparing an acellular soft tissue graft for implantation into a mammalian system, including inducing a pressure mediated flow of an extracting solution including one or more nonionic detergents and one or more endonucleases, through soft tissue, to produce extracted tissue; inducing a pressure mediated flow of a treating solution including one or more anionic detergents, through the extracted tissue, to produce a treated tissue; inducing a pressure mediated flow of a decontaminating solution including one or more decontaminating agents through the treated tissue, to produce the acellular soft tissue graft; and storing the acellular soft tissue graft in a storage solution including one or more decontaminating agents.

The invention provides a process where the extracting solution is recirculated through the soft tissue graft.

The invention further provides a process where the treating solution is recirculated through the soft tissue graft.

The invention also provides a process where the decontaminating solution is recirculated through the soft tissue graft.

The invention provides a process for producing an acellular tissue graft and includes the use of calcium salts which use results in the acellular tissue graft containing a significantly more insoluble form of salt precipitated anionic detergent, which results in retarded recellularization of the acellular tissue graft in vivo or in vitro.

BRIEF DESCRIPTION OF THE DRAWINGS

FIG. 7 is a bar graph illustrating the percent reduction in nucleic acids extractable from human saphenous veins using the inventive process.

FIGS. 8A & 8B are graphs illustrating the binding of a nonionic detergent, tritiated Triton X-100, to human saphenous vein versus time of incubation.

FIGS. 9A & 9B are graphs illustrating the release of a nonionic detergent, tritiated Triton X-100, from human saphenous vein versus time of incubation.

FIGS. 10A & 10B are graphs illustrating the binding of an anionic detergent, tritiated sodium dodecylsulfate, to human saphenous vein versus time of incubation.

DETAILED DESCRIPTION OF THE PREFERRED EMBODIMENTS

Figure 1:
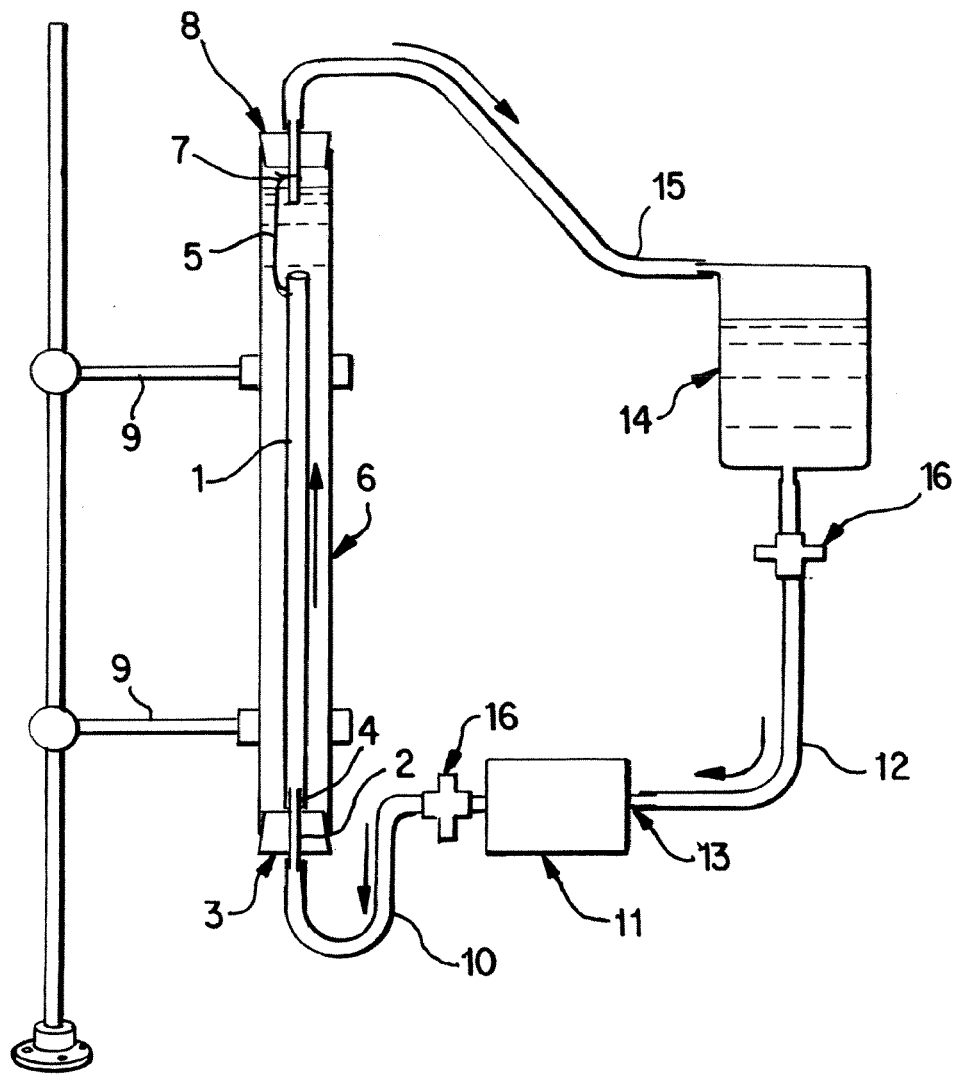
FIG. 1 illustrates a view of one embodiment of the processing chamber showing flow mediated processing of long vein segments.

Definitions. The below definitions serve to provide a clear and consistent understanding of the specification and claims, including the scope to be given such terms.

Allowash™ Solution.

By the term "Allowash™ solution" is intended those compositions disclosed in U.S. Pat. No. 5,556,379 incorporated herein by reference. Examples of suitable Allowash™ compositions include: A cleaning composition containing about 0.06 wt % polyoxyethylene-4-lauryl ether; about 0.02 wt % poly (ethylene glycol)-p-nonyl-phenyl-ether; about 0.02 wt % octylphenol-ethyleneoxide and endotoxin free deionized/distilled water.

Decontaminating Agent.

By the term "decontaminating agent" is intended one or more agents which remove or inactivate/destroy any infectious material potentially present in a biological tissue sample, for example, such agents include but are not limited to one or more of the following: an antibacterial agent; an antiviral agent; an antimycotic agent; an alcohol for example, methyl, ethyl, propyl, isopropyl, butyl, and/or t-butyl; trisodium phosphate; a preservative such as chlorine dioxide, isopropanol, METHYLPARABIN® (Croda, Inc.), antimicrobials, antifungal agents, sodium hydroxide; hydrogen peroxide; a detergent, and ultrapure water, where the decontaminating agent or agents do not chemically alter the matrix components of the soft tissue grafts.

Essentially Free From.

By the term "Essentially Free From" is intended for the purposes of the present invention, a soft tissue graft where the material removed (for example, cellular elements and infectious materials) from the soft tissue graft is not detectable using detection means known in the art at the time of filing of this application.

Normal Tissue.

By the term "normal tissue" is intended for the purposes of the present invention, a particular soft tissue, for example a vein, artery, heart valve, ligament, tendon, fascia, dura mater, pericardium or skin, present in a living animal, including for example a human, a pig, and/or a cow. Tensile properties of a particular decellularized soft tissue graft approximate, that is, are not statistically significantly different from, the tensile properties of that tissue in a living animal. Cellular components of soft tissue graft biomaterials represent the major immunogenic component of such grafts post implantation.

Acellular Soft Tissue Graft.

By the term "acellular tissue graft" is intended for the purposes of the present invention, soft tissue including but not limited to veins, arteries, heart valves, ligaments, tendons, fascia, dura matter, pericardium, and skin, from any mammalian source, including but not limited to, a human source, porcine source, and a bovine source, where the acellular graft produced is allogenic or xenogenic to the mammalian recipient.

The invention provides a process for removing these cellular components from the tissue without resultant damage to the matrix and/or tissue structure. Preferably, the tissue thickness does not exceed about 8 mm, more preferably does not exceed about 6 mm, and most preferably does not exceed about 4 mm, such that the time intervals described herein are sufficient for the process solutions to penetrate the tissue and solubilize the cellular components, allowing for the extraction of extractable materials. Processing times can be altered to accommodate thicker tissues. A quantity of endonuclease is used for a given volume of tissue, such that the quantity is sufficient to digest the DNA within that volume of tissue.

The invention recognizes that the mechanical strength of soft tissue graft biomaterials resides in the matrix structure of the graft. The matrix structure of these biomaterials include collagens, elastins, mucopolysaccharides and proteoglycan components. The removal of cellular components from the graft does not compromise the mechanical strength of the graft. The invention further recognizes that vascular and non-vascular soft tissue grafts do not need to be readily repopulated by recipient cells, post implantation, to function long-term. The absence of an early and rapid repopulation event(s) results in a graft having adequate mechanical strength similar to the mechanical strength associated with that particular normal tissue. This is because the subsequent remodeling of a graft is associated with weakening of the mechanical strength of the graft. That treatment of the graft with a strongly anionic detergent, such as sodium dodecylsulfate, leaves a strongly anionic charge distribution to the graft. This, in turn, restricts recellularization of the graft post implantation. Further, differences in anionic detergent binding to basement membrane components of the graft allows early re-endothelialization of vascular graft(s). That slow leaching of the anionic detergent from the graft allows slow long-term repopulation and slow long-term remodeling of the transplanted soft tissue graft consistent with a durability and graft life, to be measured in terms of decades. Although the description of the invention is directed primarily at processing vascular graft materials, it should be appreciated that this invention is not restricted to processing of vascular graft materials and can also be directed to processing non-vascular soft tissue grafts. Such tissue grafts include, but are not limited to, tissues such as tendons, fascia, ligaments, pericardium, intestine, skin, dura, and cartilage. Such soft tissue can be processed by one of ordinary skill in the art to which the present invention pertains by simple manipulation of the inventive processing times, without undue experimentation.

Tissue is processed according to the invention by surgically removing normal healthy tissues (for example, veins, arteries, heart valves) from animals or humans. The removed tissue is then transported to a processing facility where the tissue is cleaned of extraneous matter and quickly submersed in the first processing (extracting) solution which includes hypotonic buffered solutions containing an endonuclease, for example Benzonas®, and nonionic detergent(s) including for example Allowash Solution™, TritonX-100, and/or Tween 20, and $MgCl_2$ Other suitable nonionic detergents can be readily selected and employed by one of ordinary skill in the art to which the present invention pertains, without undue experimentation. Procurement and transport of tissue is preferably carried out sterilely and is held in a sterile container on wet ice in a solution iso-osmolar to the cellular population of the tissue being procured and transported. Furthermore, antibiotics may be added to the procurement and transport solution. The invention includes the use of one or more decontaminating agents including for example one or more antibiotics, anti-fungal agents or anti-mycotic agents. Other such agents can be added during processing if so desired to maintain sterility of the procured tissues.

According to an aspect of the invention, a process for preparing biological material for implantation into a mammalian cardiovascular system, musculoskeletal system, or soft tissue system, or for recellularization in vitro, is provided and includes removing cellular membranes, nucleic acids, lipids, and cytoplasmic components, and forms an extracellular matrix including collagens, elastins, proteoglycans, and mucopolysaccharides, the process includes, isolating from a suitable donor a desired tissue sample of the biological material; extracting the tissue with mildly alkaline hypotonic buffered solution of an endonuclease (including for example Benzonase® (a registered product of Merck KGaA, Darmstadt, Germany)) and a nonionic detergent formulation (including for example Allowash Solution™ (a product of LifeNet, Virginia Beach, Va.)); treating the tissue with a mildly alkaline hypotonic buffered solution of an anionic detergent (including for example sodium dodecylsulfate); washing the tissue with water followed by a water or isotonic saline solution of chlorine dioxide or alcohol wash; and storage in a sealed container in water (for example, ultrapure water) or a dilute isotonic solution which may contain low concentrations of chlorine dioxide or 70% isopropanol.

The cellular components of soft tissue graft biomaterials represent the major immunogenic component of such grafts post implantation and the invention provides for the removal of these cellular components without resultant damage to the matrix structure in which the cells resided. Preferably, the soft tissue sample thickness does not exceed about 4 mm such that the time intervals described herein are sufficient for the solutions to penetrate and affect the necessary solubilization and extraction of extractable materials. The concentration of endonuclease utilized is based on calculations designed at achieving a sufficient quantity of endonuclease within a given volume of tissue which is sufficient to digest the DNA within that volume of tissue and is not arbitrarily chosen based on volume of processing solution. The inventive process maintains the mechanical strength of the soft tissue graft biomaterials because the process does not detrimentally affect the matrix structure of the graft. The matrix structure of these biomaterials include collagen, elastin, mucopolysaccharide and proteoglycan components.

The inventive process provides for the modulation of recellularization of the acellular soft tissue graft by adjusting the amount of bound and/or precipitated anionic detergent left in the acellular soft tissue graft produced.

This invention provides for the production of vascular and tendenous grafts, which are not repopulated by recipient cells, post implantation. The inventors discovered that these grafts do not need to be repopulated to function long-term. That absence of repopulation events reduce the possibility that subsequent remodeling of the graft will occur along with the weakening of mechanical strength of the graft which would be associated with remodeling. That treatment of the graft with a strongly anionic detergent, such as sodium dodecylsulfate, will leave a strongly anionic charge distribution to the graft that will restrict recellularization of the graft post implantation and that differences in SDS binding to the basement membrane components will allow reendothelialization of the vascular graft(s).

The inventors further discovered that the introduction of high salt concentrations in the tissues prior to or following treatment/extraction with an anionic detergent such as SDS results in the precipitation of greater quantities of this anionic detergent within the tissues and that this greater quantity of anionic detergent significantly restricts recellularization of the acellular tissue graft, than treatment of the tissue sample with an anionic detergent without the use of high salt concentrations in that tissue.

The invention provides a process that uses 0.001% to 0.024% anionic detergent, for example, SDS in the treatment phase which causes deposition of SDS in the tissues without the potentially harmful effects of using 1% SDS in the treatment phase and can be used preferentially with or without introduction of high salt concentrations in the tissue when recellularization of that tissue is desired. Although the description of this invention is directed primarily at processing vascular graft materials, it should be appreciated that this invention can also be directed to processing non vascular soft tissue grafts such as tendons, fascia, ligaments, pericardium, skin, dura, and cartilage by simple manipulation of processing times and parameters, such manipulation can be readily determined and employed by one of ordinary skill in the art, without undue experimentation.

In the inventive process, normal healthy vessels (veins, arteries, heart valves, tendons, ligaments, fascia, pericardium, intestine, urethra, etc.) are surgically removed from animals or humans, transported to the processing facility where they are cleaned of extraneous matter and immediately submersed in an extracting solution which contains a hypotonic buffered solution containing one or more endonucleases including for example, Benzonase, and one or more nonionic detergents including for example, Allowash Solution, Triton X-1100, and Tween 20. In that most such vessels are procured at sites distant from the processing facility and that such vessels may ultimately either be cryopreserved or made acellular, procurement and transport will normally be in a sterile container on wet ice in a solution isoosmolar to the cellular population of the tissue being procured and transported. Furthermore, antibiotics are preferably added to the procurement and transport solution. One or more decontaminating agents, including for example, one or more antibiotics, can be optionally employed in any step of the inventive process, to maintain sterility of the procured tissues.

FIG. 1 illustrates the processing of a long vein grafts (1), the distal end of the vein is cannulated onto the ribbed attachment (2) of the inlet port (3) and a single suture (4) is used to secure the vein. An additional suture line (5) is attached to the proximal end of the vein for later use in maintaining the vein in an extended state in the processing vessel (6). The vein (1) is then removed from the first processing (extracting) solution and transferred to the processing vessel (6) that has been temporarily inverted. The second suture line (5) along with the vein (1) is passed through the processing vessel (6) and secured to a point (7) on the outlet port end (8) of the processing vessel (6). Prior to closing the processing vessel, a portion of the first processing (extracting) solution is gently added to the processing vessel and the inlet port (3), with attached vein (1), is then secured. The processing vessel (6) is turned such that the inlet port (3) is down and the outlet port (8) is up and the vessel (6) is attached to its support racking system via clamps (9). Sterile disposable tubing (10) is attached to the inlet port (3) and to pump tubing in a peristaltic pump (11). Further, sterile disposable tubing (12) is attached to the inflow side (13) of the peristaltic pump (1) and to the solution reservoir (14) which will contain all remaining first processing (extracting) solution. Finally, sterile disposable tubing (15) is attached between the top (outlet) port (8) of the processing vessel (6) and the solution reservoir (14). Sterile, in-line, filters (16) can optionally be added at appropriate positions in the fluid flow to safeguard sterility during processing. The first processing (extracting) solution is pumped into, through and out of the processing vessel (6) such that flow of fluids through the luminal part of the vein tubule passes into the processing vessel (6) to affect constant solution change in the processing vessel and out through the outlet port (8) to a solution reservoir (14). By processing the vein in an inverted state, air which may be trapped in the luminal space of the vein will be induced to exit facilitating equal access of the processing solutions to the vein tissue being processed. Processing of the vein tissue with the first processing (extracting) solution is preferably carried out at temperatures ranging from about 4° C. to about 37° C. for time periods ranging from about one hour to about 24 hours (overnight as necessary to accommodate processing scheduling of processing staff). The endonuclease (Benzonase) is optimally active between pH 6 and 10, and from 0° C. to above 42° C. (Merck literature describing product) when provided with 1-2 mM $Mg^{+2}$ Following processing with the first processing (extracting) solution, the first processing solution can optionally be replaced with water, for example sterile ultrapure water, to preclude a possible precipitation reaction between the nonionic detergents in the first processing (extracting) solution and the anionic detergent in the second processing (treating) solution, or the first processing (extracting) solution can be replaced with an alkaline hypotonic solution containing one or more detergents, including for example, sodium dodecylsulfate (SDS) at a concentration, for example, of about 1% by weight (second processing (treating) solution). Under the optional processing procedure, only sufficient water need be circulated through the processing vessel to affect one volume change of solution in the processing vessel. During processing with the second processing (treating) solution, this solution is circulated through the tissue, preferably at a temperature of from room temperature to about 37° C., to avoid precipitation of the detergent, for example SDS, at reduced temperatures, for a time period not shorter than 3 hours. Following processing with the second processing (treating) solution, water, for example ultrapure sterile water, is circulated through the tissue and processing vessel such that the available volume of washing solution approximates a 1000-fold dilution of the detergent, for example SDS, present in the second processing (treating) solution. The SDS will exit from the tissues to a given amount of SDS/mg tissue wet weight (protein concentration) provided the washing time is at least 1 hour, preferably at least 2 hours and more preferably at least 3 hours, at a flow rate sufficient to affect a volume change in the processing vessel about every 30-40 minutes, suitable flow rates including for example of from about 30 mls/min. to about 70 mls/min., more preferably from about 40 mls/min to about 60 mls/min., and most preferably about 50 mls/min. Following washing in this final processing step, the vein is removed from the processing vessel and transferred into storage solution, for example phosphate buffered saline, 70% isopropanol, or 0.001% to 0.005% chlorine dioxide in sterile ultrapure water/isotonic saline, and packaged in a volume of storage solution sufficient to cover the tissue preventing dehydration. This packaged graft may then be terminally sterilized, for example using gamma irradiation, if so desired. Artery segments can be similarly processed, taking into consideration that veins have valves and arteries do not, and that veins generally have a smaller internal diameter than arteries, thus dictating slower flow rates with veins.

Figure 2:
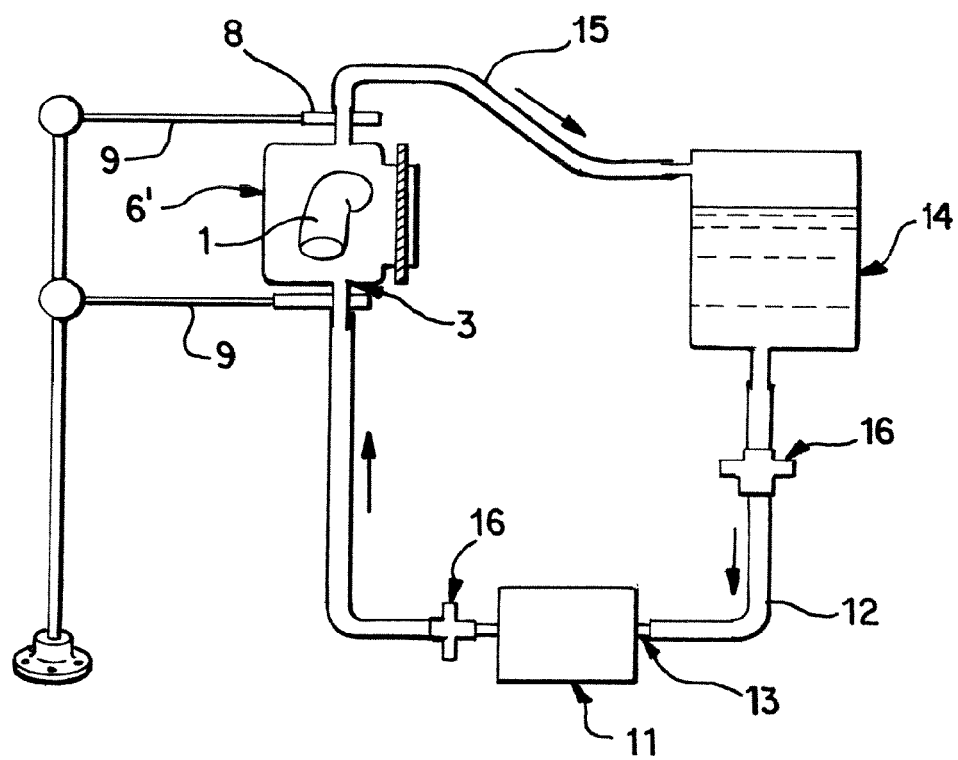
FIG. 2 illustrates a view of an embodiment of the processing chamber showing flow mediated processing of a heart valve.
Figure 3:
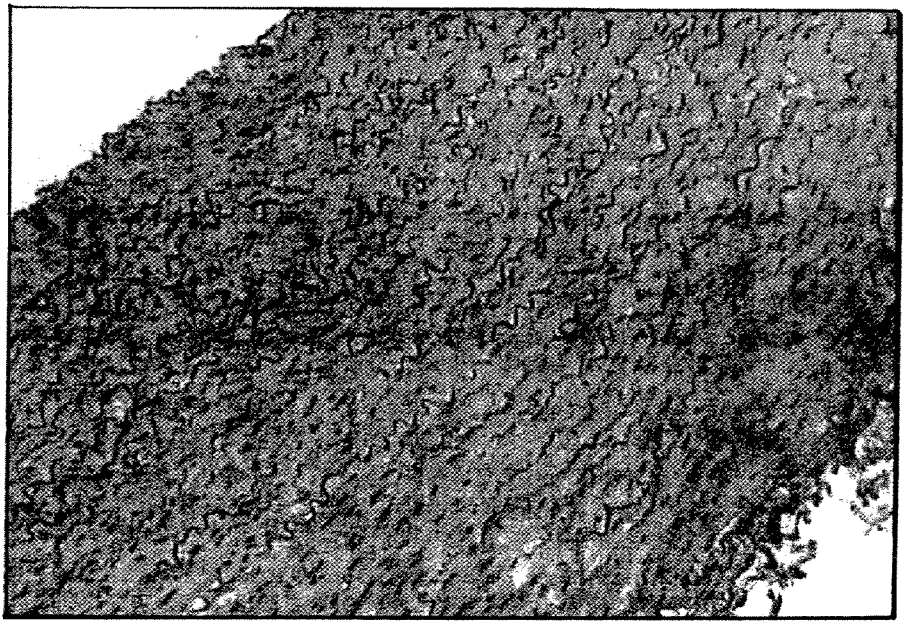
FIG. 3 illustrates a view of an unprocessed human saphenous vein examined with Hemoxylin and Eosin staining, magnified 20 times.
Figure 4:
FIG. 4 illustrates a view of an unprocessed human saphenous vein examined with Feulgen staining, magnified 20 times.
Figure 5:
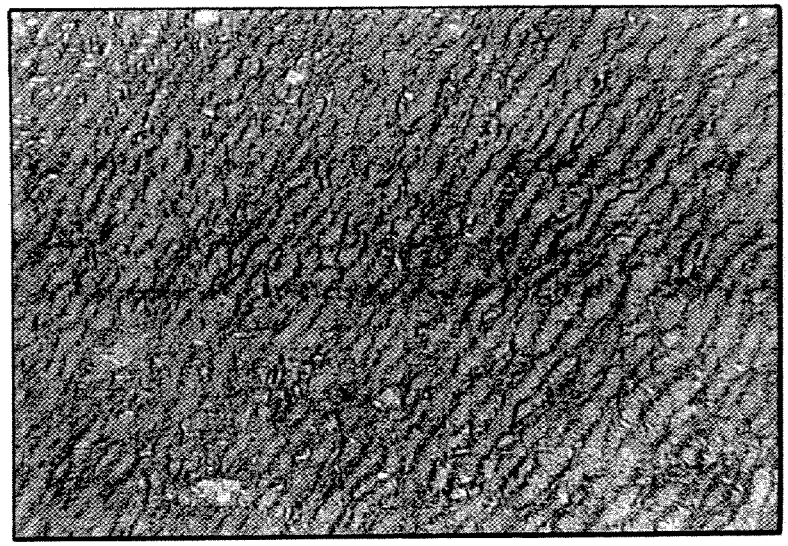
FIG. 5 illustrates a view of a decellularized human saphenous vein examined with Hemoxylin and Eosin staining, magnified 20 times.
Figure 6:
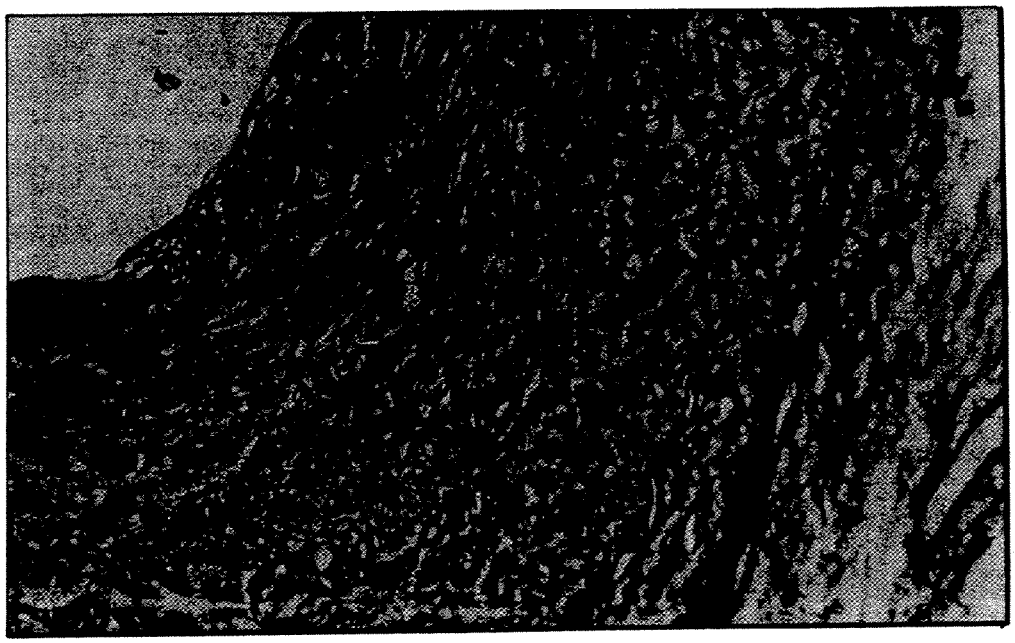
FIG. 6 illustrates a view of a decellularized human saphenous vein examined with Feulgen staining, magnified 20 times.
Figure 10B:
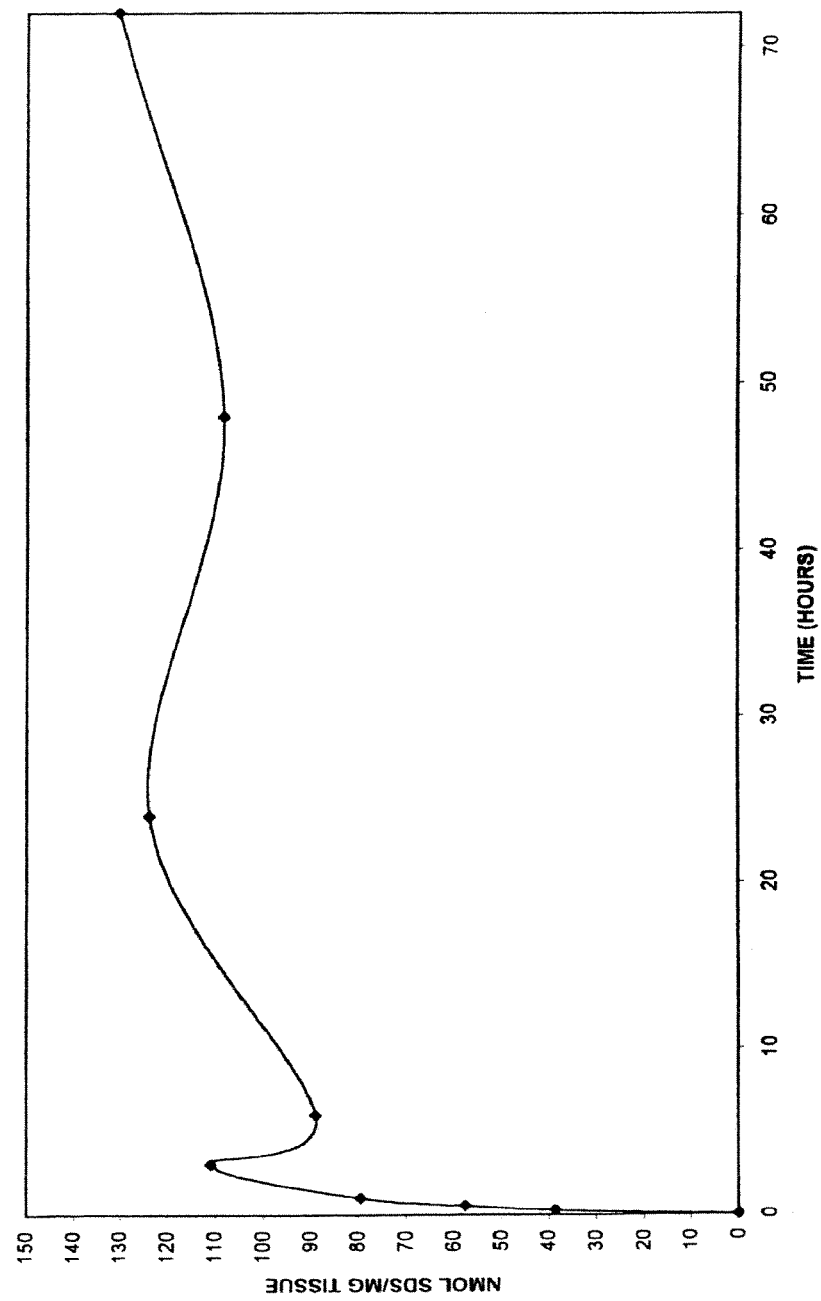
Figure 11A:
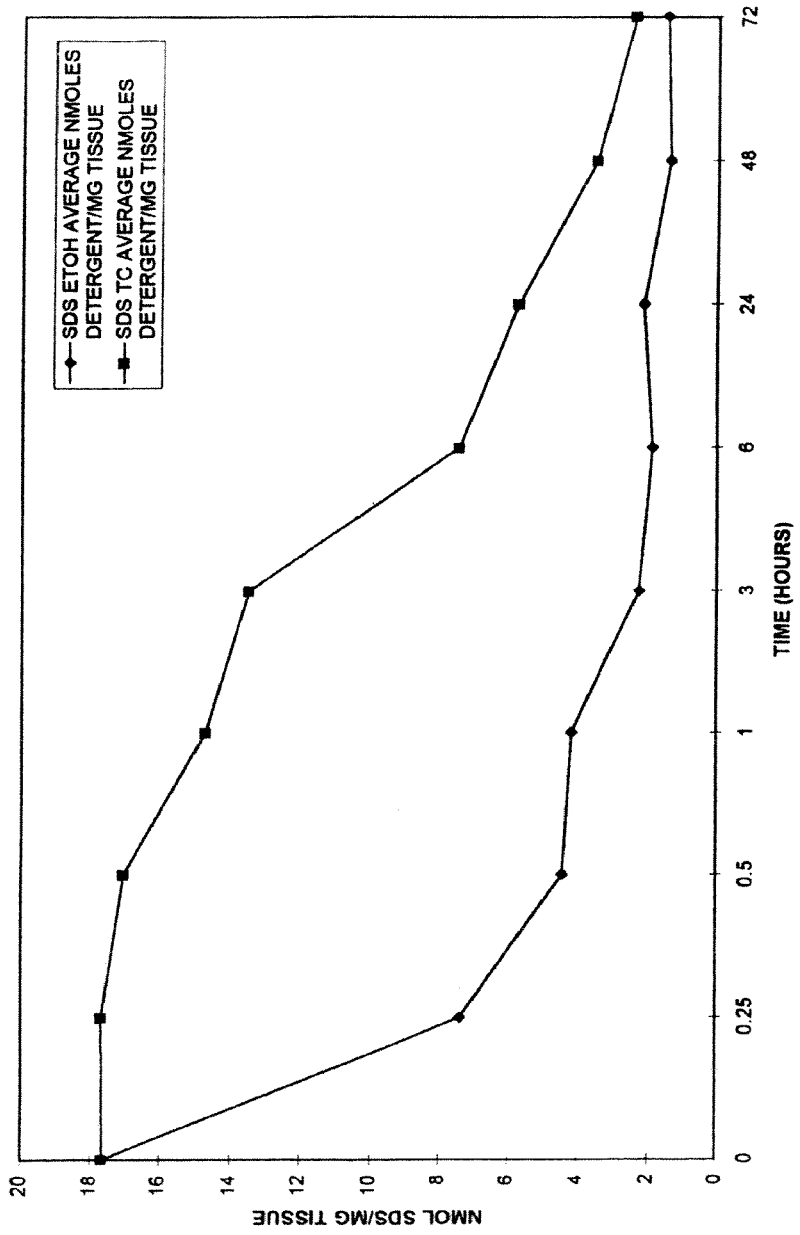
FIGS. 11A & 11B are graphs illustrating the release of an anionic detergent, tritiated sodium dodecylsulfate, from human saphenous vein versus time of incubation.
Figure 11B:
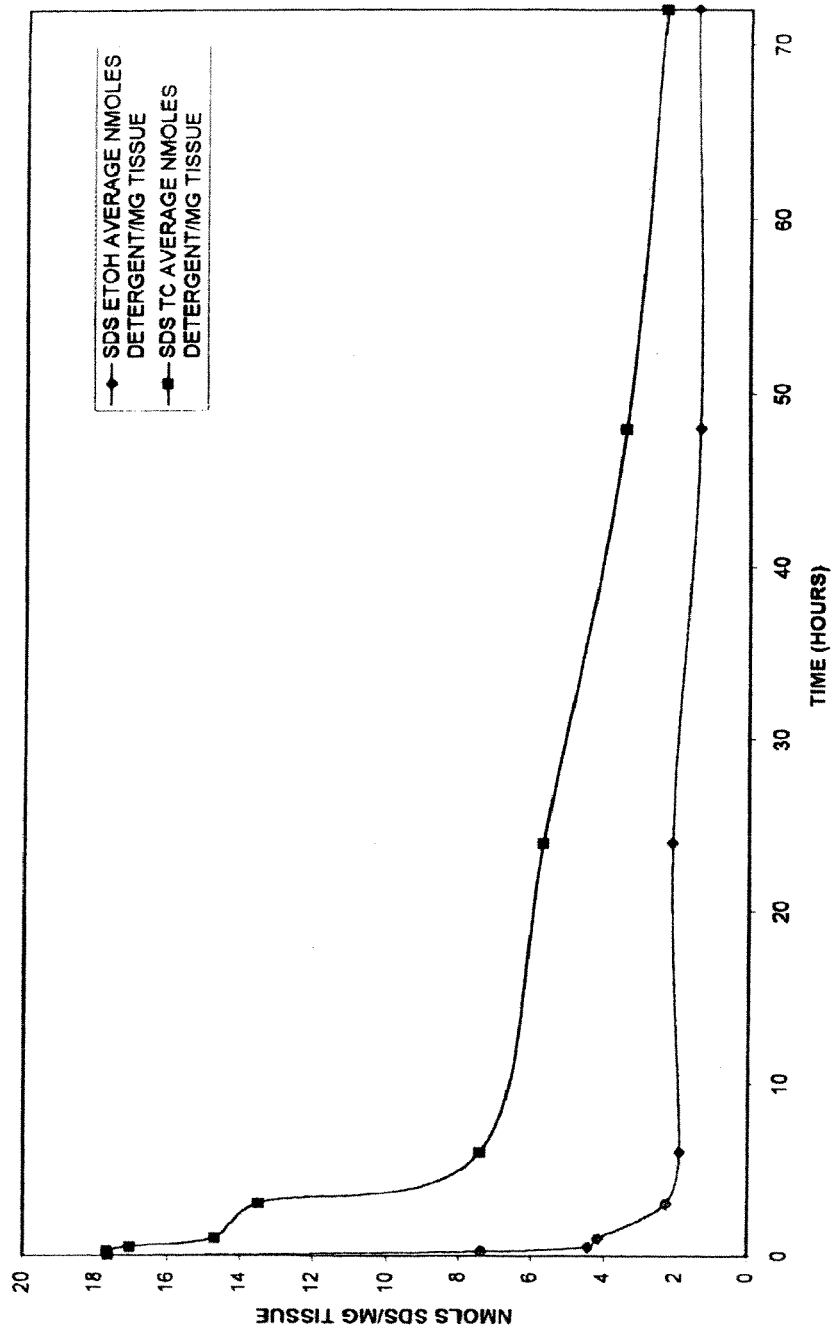
Figure 12A:
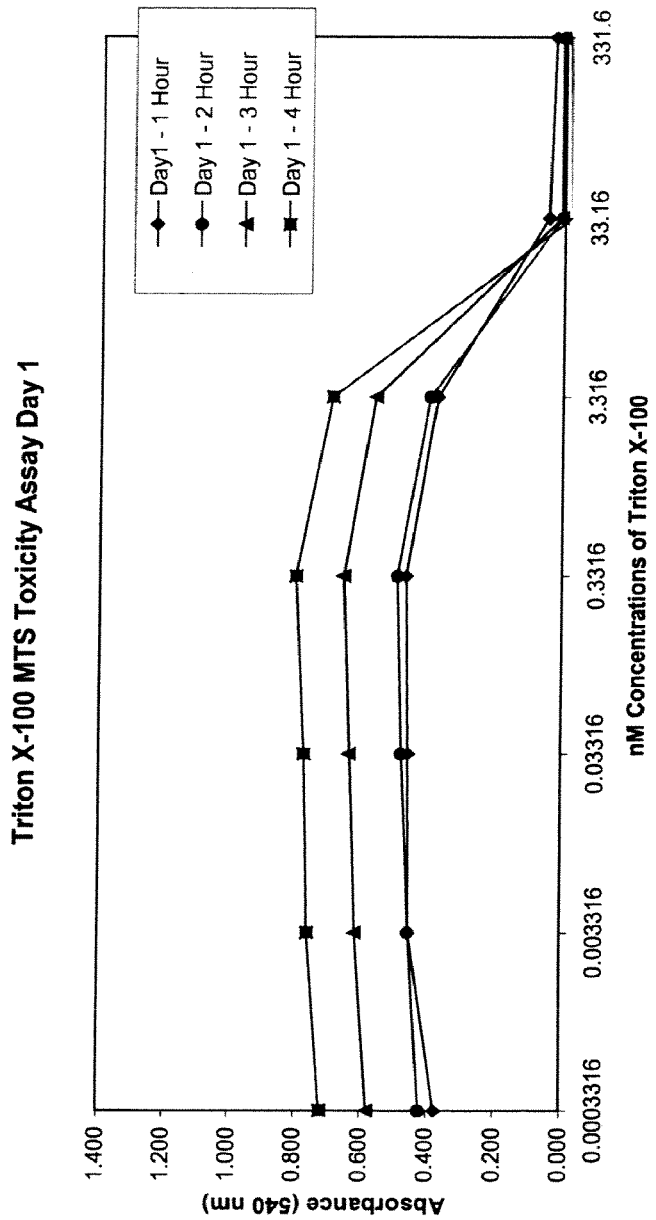
FIGS. 12A & 12B are graphs illustrating the toxicity of a nonionic detergent, Triton X-100, towards mammalian cells in in vitro culture, on days 1 and 7, respectively.
Figure 12B:
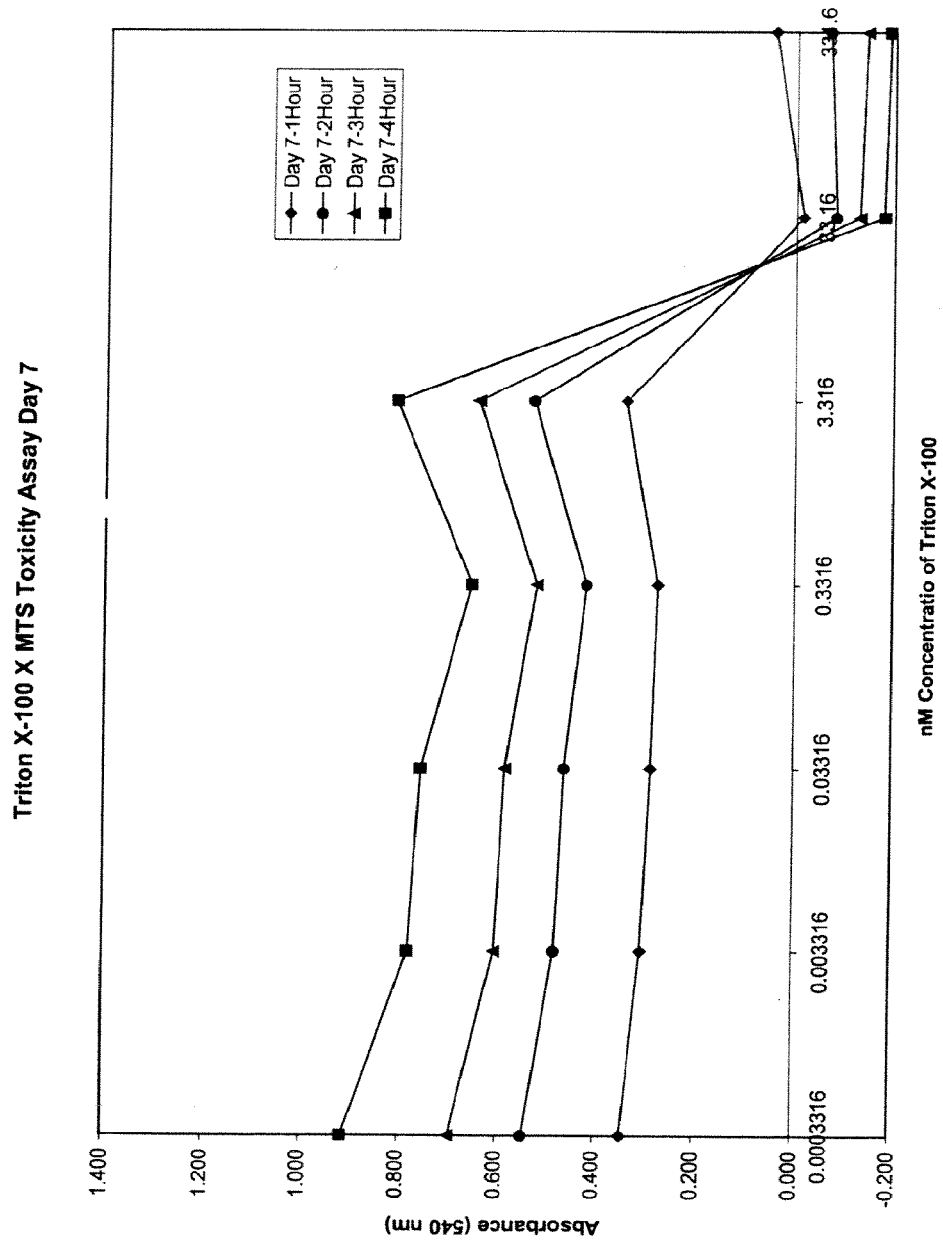
Figure 13A:
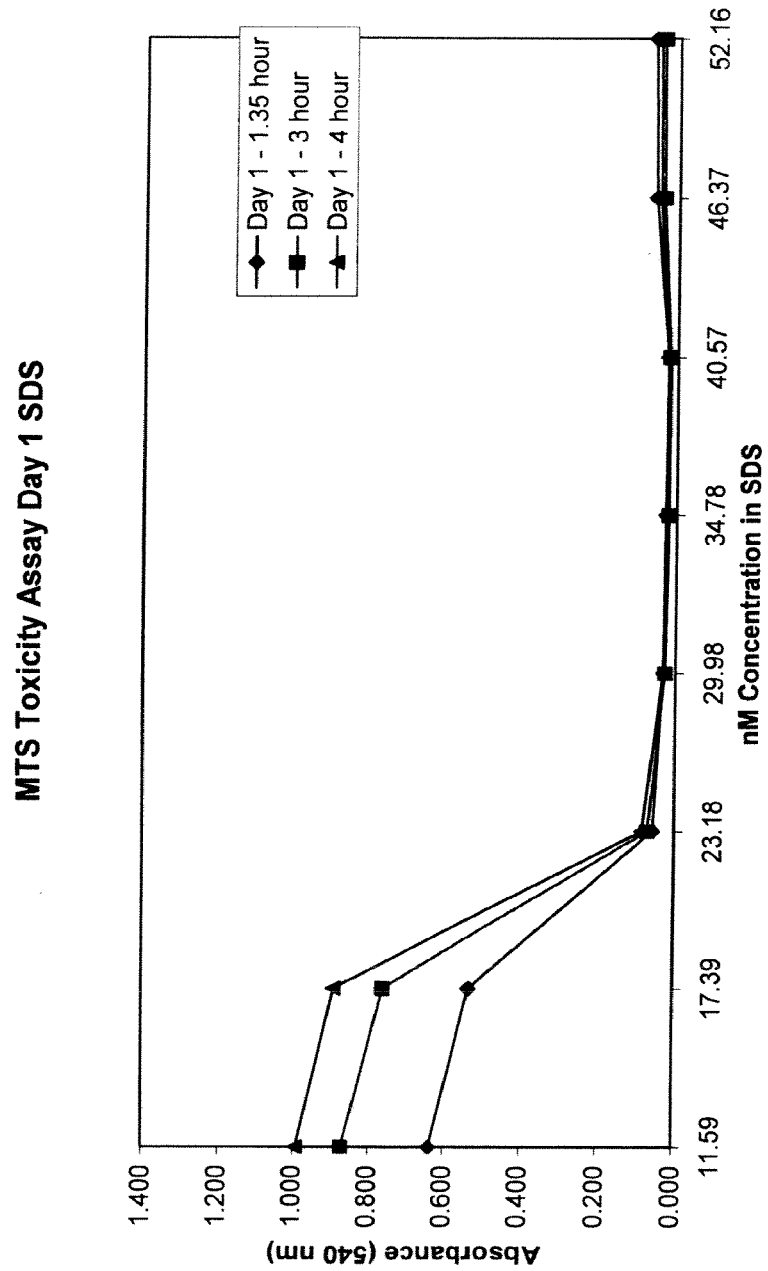
FIGS. 13A & 13B are graphs illustrating the toxicity of an anionic detergent, sodium dodecylsulfate, towards mammalian cells in in vitro culture, on days 1 and 7, respectively.
Figure 13B:
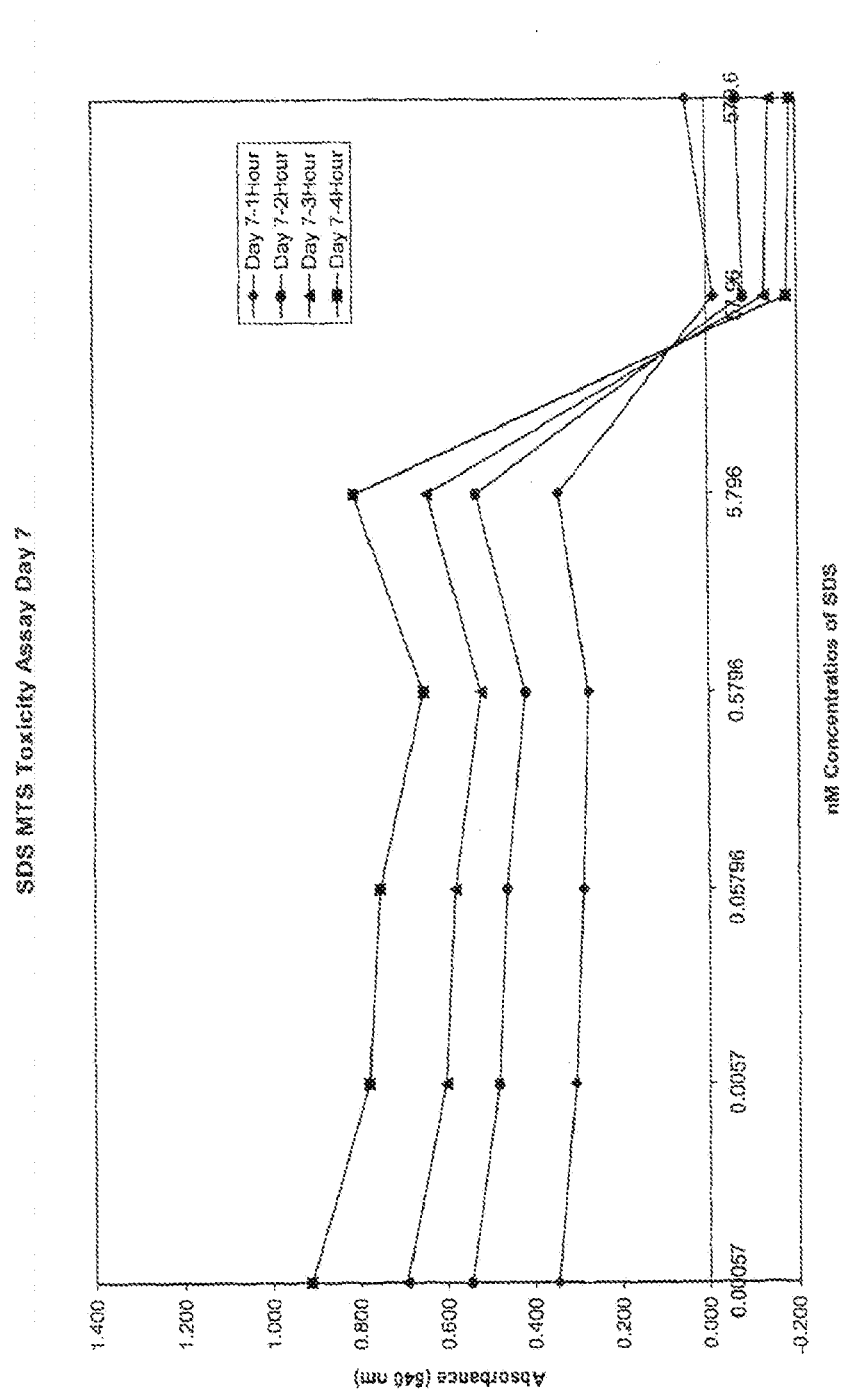
Figure 14:
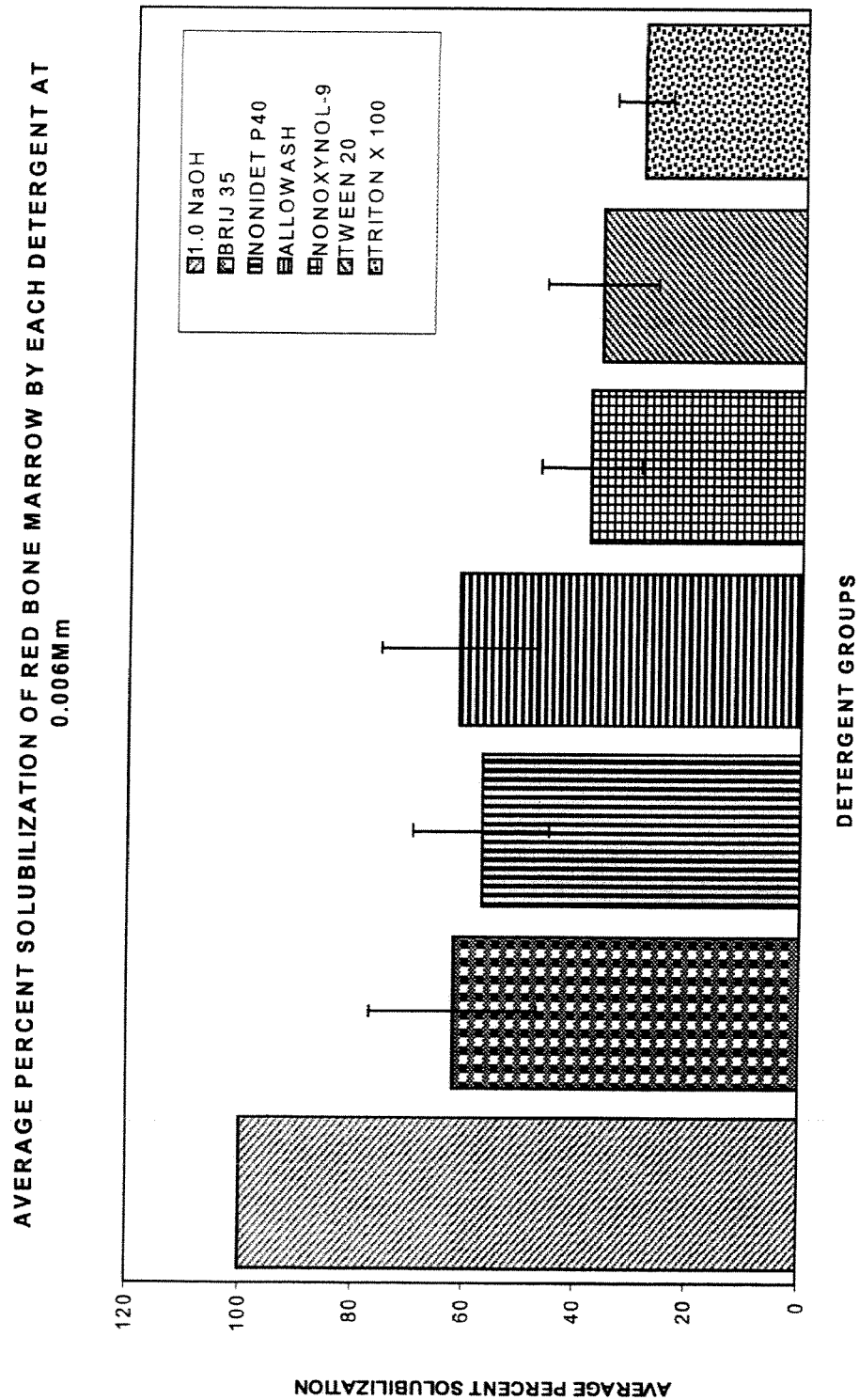
FIG. 14 is a graph illustrating the ability of detergents to disrupt and solubilize mammalian cells.

FIG. 2 illustrates processing heart valve grafts. The heart valve (1) is placed into the deformable processing device (2) such that the valved end of the conduit is directed towards the inlet port (3) and the nonvalved end of the conduit is directed towards the outlet port (8). Prior to closing the processing vessel (2), a portion of the first processing (extracting) solution is gently added to the processing vessel. The processing vessel (2) is turned such that the inlet port (3) is down and the outlet port (8) is up to effect removal of air bubbles, and the vessel (2) attached to its support racking system via clamps (9). Sterile disposable tubing (10) is attached to the inlet port (3) and to pump tubing in a peristaltic pump (1). Further, sterile disposable tubing (12) is attached to the inflow side (13) of the peristaltic pump (11) and to the solution reservoir (14) which will contain all remaining first processing (extracting) solution. Finally, sterile disposable tubing (15) is attached between the top (outlet) port (8) of the processing vessel (2) and the solution reservoir (14). Sterile, in-line, filters (16) can optionally be added at appropriate positions in the fluid flow to safeguard sterility during processing. The first processing (extracting) solution is pumped into, through and out of the processing vessel (2) such that the flow of fluids through the luminal part of the heart valve (1) passes into the processing vessel (2) to affect constant solution change in the processing vessel (2) and out through the outlet port (8) to a solution reservoir (14). By processing the heart valve (1) in this orientation, air which may be trapped in the luminal space of the valve will be induced to exit facilitating equal access of the processing solutions to the valve tissue being processed. Processing of the heart valve (1) tissue with the first processing (extracting) solution is performed at for example, a temperature of from about 4° C. to about 37° C., for example for time periods of from about one hour to about 24 hours (overnight as necessary to accommodate processing scheduling of processing staff). The endonuclease (Benzonase) is optimally active between pH 6 and 10, and from 0° C. to above 42° C. (Merck literature describing product) when provided with 1-2 mM $Mg^{+2}$. Following processing with the first processing (extracting) solution, the first processing (extracting) solution is optionally be replaced with water, for example sterile ultrapure water, to preclude a possible precipitation reaction between the nonionic detergents in the first processing (extracting) solution and the anionic detergent in the second processing (treating) solution, or the first processing (extracting) solution can be replaced with an alkaline hypotonic solution containing for example, about 1% by weight of a detergent, for example, sodium dodecylsulfate (SDS) (second processing (treating) solution). Under the optional processing procedure, only sufficient water need be circulated through the processing vessel to affect one volume change of solution in the processing vessel. The second processing (treating) solution is circulated through the tissue at a temperature for example, of from about room temperature to about 37° C., to avoid precipitation of the detergent, for example SDS, at reduced temperatures, for a time period of for example, not shorter than 3 hours. Following processing with the second processing (treating) solution, water, for example ultrapure sterile water, is circulated through the tissue and processing vessel such that the available volume of washing solution approximates a 1000-fold dilution of the SDS present in the second processing (treating) solution. The SDS will exit from the tissues to a given amount of SDS/mg tissue wet weight (protein concentration) provided the washing time preferably exceeds 1 hour, more preferably exceeds 2 hours, and most preferably exceeds about 3 hours, at a flow rate sufficient to affect a volume change in the processing vessel about every 30-40 minutes, suitable flow rates including for example of from about 30 mls/min. to about 70 mls/min., more preferably from about 40 mls/min to about 60 mls/min., and most preferably about 50 mls/min. Following washing, the heart valve may then be removed from the processing vessel and transferred into storage solution of for example, either 70% isopropanol or 0.001% chlorine dioxide in sterile ultrapure water, and packaged in a volume of storage solution sufficient to cover the tissue preventing dehydration. Alternatively, the storage solutions can be pumped into the processing vessel until the water wash solution has been adequately exchanged and the whole processing vessel sealed and used as the storage container for distribution.

For all other soft tissue grafts, the tissue is placed into the deformable processing device such that the smaller portion is directed towards the inlet port and the larger (bulkier) end of the tissue is directed towards the outlet port. Preferably the thickness of other soft tissue grafts does not exceed about 8 mm, more preferable does not exceed 5 mm, and most preferably the thickness does not exceed about 2-3 mm. If the thickness of the tissue graft exceeds about 5 mm, incubation and processing times need to be appropriately extended. Such incubation and processing times can be readily selected and employed by one of ordinary skill in the art to which the present invention pertains based on the thickness of the tissue being processed, the type of tissue being processed, and the volume of tissue being processed, without undue experimentation. Prior to closing the processing vessel, a portion of the first processing (extracting) solution is gently added to the processing vessel. The processing vessel is then turned such that the inlet port is down and the outlet port is up and the vessel is attached to its support racking system for example, via clamps. Sterile disposable tubing is attached to the inlet port and to pump tubing in a peristaltic pump. Further, sterile disposable tubing is attached to the inflow side of the peristaltic pump and to the solution reservoir which will contain all remaining first processing (extracting) solution. Finally, sterile disposable tubing is attached between the top (outlet) port of the processing vessel and the solution reservoir. Sterile, in-line, filters can optionally be added at appropriate positions in the fluid flow to safeguard sterility during processing. The first processing (extracting) solution is pumped into, through and out of the processing vessel such that flow of fluids occurs in close proximity to the surfaces of the soft tissue grafts into the processing vessel to affect constant solution change in the processing vessel and out through the outlet port to a solution reservoir. By processing the soft tissue graft in this orientation, the bulkier portions of the soft tissue graft will receive the greatest flow of fluids across the surfaces facilitating equal access of the processing solutions to the tissue being processed. Processing of the soft tissue graft with the first processing (extracting) solution is preferably performed at a temperature of from about 4° C. to about 37° C., for a period of time preferably of from about one hour to about 24 hours (overnight as necessary to accommodate processing scheduling of processing staff). The endonuclease (Benzonase) is optimally active between pH 6 and 10, and from 0° C. to above 42° C. (Merck literature describing product) when provided with 1-2 mM $Mg^{+2}$. Following processing with the first processing (extracting) solution, the first processing (extracting) solution is optionally be replaced with water, for example sterile ultrapure water, to preclude a possible precipitation reaction between the nonionic detergents in the first processing (extracting) solution and the anionic detergent in the second processing solution, or the first processing (extracting) solution can be replaced with an alkaline hypotonic solution containing for example, preferably about 1% by weight of a detergent, for example, preferably sodium dodecylsulfate (SDS) (second processing (treating) solution). Under the optional processing procedure, only sufficient water need be circulated through the processing vessel to affect one volume change of solution in the processing vessel. The second processing (treating) solution is circulated through and/or around the tissue at a temperature of preferably form room temperature to about 37° C., to avoid precipitation of the detergent, for example SDS, at reduced temperatures, for a time period of preferably not shorter than 3 hours. Following processing with the second processing (treating) solution, water for example ultrapure sterile water, is circulated through and/or around the tissue and processing vessel such that the available volume of washing solution approximates a 1000-fold dilution of the SDS present in the second processing (treating) solution. The SDS will exit from the tissues to a given amount of SDS/mg tissue wet weight (protein concentration) provided the washing time preferably exceeds 1 hour, more preferably exceeds 2 hours and most preferably exceeds 3 hours, at a flow rate sufficient to affect a volume change in the processing vessel about every 30-40 minutes, suitable flow rates including for example of from about 30 mls/min. to about 70 mls/min., more preferably from about 40 mls/min to about 60 mls/min., and most preferably about 50 mls/min. Following washing, the soft tissue graft may be removed from the processing vessel and transferred into storage solution containing for example, buffered isotonic saline, 70% isopropanol, or 0.001% to 0.005% chlorine dioxide in sterile ultrapure water/isotonic saline, and packaged in a volume of storage solution sufficient to cover the tissue preventing dehydration. Alternatively, the storage solutions can be pumped into the processing vessel until the ultrapure water wash solution has been adequately exchanged and the whole processing vessel sealed, sterilized for example using gamma-irradiation, and used as the storage container for distribution. Storage of processed soft tissue grafts should be in a solution which covers the graft and which is contained in a container that will prevent evaporation and fluid loss or concentration of solutes. The solution can be isotonic saline, isotonic saline or ultrapure water containing a preservative such as chlorine dioxide, isopropanol, METHYLPARABIN® (Croda, Inc.), antibiotics, antimicrobials, antimycotic agents, antifungal agents, or ultrapure water, or similar bacteriostatic or bacteriocidal agent which do not chemically alter the matrix components of the soft tissue grafts. Suitable storage solutions are well known to of ordinary skill in the art to which the present invention applies, and such solutions can be readily selected and employed by those of ordinary skill in the art to which the present invention applies without undue experimentation. The storage containers with solution and soft tissue grafts can be terminally sterilized, for example using gamma irradiation at doses up to 2.5 Mrads.

The following examples illustrate processing of soft tissue grafts according to the invention.

EXAMPLE 1

Saphenous vein tissues (two) from each leg of an acceptable human donor were carefully dissected under sterile conditions to remove all visible fat deposits and the side vessels were tied off using nonresorbable suture materials such that the ties did not occur in close proximity to the long run of the vessel. Sutures can restrict the decellularization process and the tissues under the sutures were removed following decellularization. For long vein grafts (40-60 cm) (FIG. 1), the distal ends of the veins were cannulated onto the ribbed attachment of the inlet port(s) and single sutures used to secure each vein. Additional suture lines were attached to the proximal ends of the veins. The veins were then removed from the dissecting solution (ultrapure water containing 50 mM Tris-HCl (pH 7.2), 5 .mu.m EDTA, and one or more antibiotics) and transferred to the processing vessel which had been temporarily inverted. The second suture line along with the vein was passed through the processing vessel and secured to a point on the outlet port end of the processing vessel. Prior to closing the processing vessel, a portion of the first processing solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. The first processing solution was then pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the first processing solution was performed at 25±5° C. for 16 hours using a flow rate of the first processing solution of 60 mls/min. The first processing (extracting) solution consisted of 50 mM Tris-HCl (pH 7.2), 5 mM $MgCl_2$, 1% (w:v) Allowash Solution (as described in U.S. Pat. No. 5,556, 379), and endonuclease (Benzonase, a registered product of EM Industries, Inc.) (41.8 Units/ml). Following processing with the first processing solution, the first processing solution was replaced with sterile ultrapure water (250 mls at a pump rate of 90 mls/min.) which was then replaced with an alkaline hypotonic solution containing about 1% by weight sodium dodecylsulfate (SDS) in ultrapure water buffered with 50 mM Tris-HCl (pH 7.2) (second processing (treating) solution). Under this processing procedure, only sufficient ultrapure water was circulated through the processing vessel to affect one volume change of solution in the processing vessel. Under the processing with second processing (treating) solution, this second solution was circulated (flow rate of 60 mls/min.) through the tissue at room temperature (25±5° C.), to avoid precipitation of the SDS at reduced temperatures, for a time period of about 3 hours. Following processing with the second processing solution, ultrapure sterile water was circulated through the tissue and processing vessel such that the available volume of washing solution approximated a 1000-fold dilution of the SDS present in the second processing solution with a flow rate of 2 ml/min. for 1.5 hours. Following washing in this final processing step, the vein was removed from the processing vessel and transferred into storage solution of 0.005% chlorine dioxide in sterile ultrapure water and packaged in a volume of this solution sufficient to cover the tissue.

EXAMPLE 2

Saphenous vein tissues (two) from each leg of an acceptable human donor were carefully dissected under sterile conditions to remove all visible fat deposits and side vessels were tied off using nonresorbable suture materials such that the ties did not occur in close proximity to the long run of the vessel. Sutures can restrict the decellularization process and the tissues under the sutures were removed following decellularization. For these long vein grafts (33 and 28 cm) (FIG. 1), the distal ends of the veins were cannulated onto the ribbed attachment of the inlet port(s) and single sutures used to secure each vein. Additional suture lines were attached to the proximal ends of the veins. At this point, the veins were removed from the dissecting solution (ultrapure water containing 50 mM Tris-HCl (pH 7.2), 5 mM EDTA, and one or more antibiotics and transferred to the processing vessel which had been temporarily inverted. The second suture line along with the vein was passed through the processing vessel and secured to a point on the outlet port end of the processing vessel. Prior to closing the processing vessel, a portion of the first processing (extracting) solution was gently added to the processing vessel and the inlet port, with attached vein, was then secured. The processing vessel was then turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing (extracting) solution. Total processing solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. The first processing (extracting) solution was pumped into, through and out of the processing vessel such that flow of fluids through the luminal part of the vein tubule passed into the processing vessel to affect constant solution chance in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the first processing (extracting) solution was performed at 25±5° C. for 16 hours using a flow rate of the first processing solution of 30 mls/min. The first processing (treating) solution consisted of 50 mM Tris-HCl (pH 7.2), 5 mM $MgCl_2$, 1% (w:v) Triton X-100, and endonuclease (Benzonase, a registered product of EM Industries, Inc.) (41.8 Units/ml). Following processing with the first processing (extracting) solution, the first processing (extracting) solution was replaced with an alkaline hypotonic solution containing about 1% by weight sodium dodecylsulfate (SDS) in ultrapure water buffered with 50 mM Tris-HCl (pH 7.2) (second processing (treating) solution). Under the processing with second processing (treating) solution, this second solution was circulated (flow rate of 120 mls/min.) through the tissue at room temperature (25±5° C.) to avoid precipitation of the SDS at reduced temperatures, for a time period of 3 hours. Following processing with the second processing solution, ultrapure sterile water was circulated through the tissue and processing vessel such that the available volume of washing solution approximated a 1000-fold dilution of the SDS present in the second processing solution with a flow rate of 1 ml/minute for 1.5 hours. Following washing in this final processing step, the vein was removed from the processing vessel and transferred into storage solution of 0.001% chlorine dioxide in sterile ultrapure water and packaged in a volume of this solution sufficient to cover the tissue.

EXAMPLE 3

Internal mammary artery tissues (two) from an acceptable human donor were carefully dissected under sterile conditions to remove all visible fat deposits and side vessels were tied off using nonresorbable suture materials such that the ties did not occur in close proximity to the long run of the vessel. Sutures can restrict the decellularization process and the tissues under the sutures were removed following decellularization. For short artery grafts (11 and 8 cm) (FIG. 1), one end of each artery were cannulated onto the ribbed attachment of the inlet port(s) and single sutures used to secure each arteries. The arteries were then removed from the dissecting solution (ultrapure water containing 50 mM Tris-HCl (pH 7.2), 5 mM EDTA, and one or more antibiotics) and transferred to the processing vessel which had been temporarily inverted. Prior to closing the processing vessel, a portion of the first processing (extracting) solution was gently added to the processing vessel and the inlet port, with attached artery, was then secured. At this point, the processing vessel was turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 150 ml. Finally, sterile disposable tubing was attached between the top (outlet) port of the processing vessel and the solution reservoir. Sterile, in-line, filters were added at appropriate positions in the fluid flow to safeguard sterility during processing. The first processing (extracting) solution was pumped into, through and out of the processing vessel such that flow of fluids through the luminal part of the artery tubule passed into the processing vessel to affect constant solution change in the processing vessel and out through the outlet port to a solution reservoir. By processing the artery in an inverted state, air which had been "trapped" in the luminal space of the vein was induced to exit facilitating equal access of the processing solutions to the vein tissue being processed. Processing of the artery tissue with the first processing (extracting) solution was performed at 25±5° C. for 16 hours using a flow rate of the first processing (extracting) solution of 50 mls/min. The first processing (extracting) solution consisted of 50 mM Tris-HCl (pH 7.2), 5 mM $MgCl_2$, 1% (w:v) Allowash Solution (as described in U.S. Pat. No. 5,556,379), and endonuclease (Benzonase, a registered product of EM Industries, Inc.) (41.8 Units/ml). Following processing with the first processing (extracting) solution, the first processing (extracting) solution was replaced with sterile ultrapure water (250 mls at a pump rate of 60 mls/min.) which was then replaced with an alkaline hypotonic solution containing about 1% by weight sodium dodecylsulfate (SDS) in ultrapure water buffered with 50 mM Tris-HCl (pH 7.2) (second processing (treating) solution). Under this processing procedure, only sufficient ultrapure water was circulated through the processing vessel to affect one volume change of solution in the processing vessel. Under the processing with second processing solution, this second solution was circulated (flow rate of 30 mls/min.) through the tissue at room temperature (25±5° C.) to avoid precipitation of the SDS at reduced temperatures, for a time period of 3 hours. Following processing with the second processing solution, ultrapure sterile water was circulated through the tissue and processing vessel such that the available volume of washing solution approximated a 1000-fold dilution of the SDS present in the second processing solution with a flow rate of 2 ml/min. for 1.5 hours. Following washing in this final processing step, the artery was removed from the processing vessel and transferred into storage solution of 70% (v:v) pharmaceutical grade isopropanol in sterile ultrapure water and packaged in a volume of this solution sufficient to cover the tissue.

EXAMPLE 4

Aortic and pulmonary tissues (one each) from a heart of an acceptable human donor were carefully dissected under sterile conditions to remove all visible fat deposits and cardiac muscle tissue (leaving only a small but visible band of cardiac muscle tissue around the proximal end of the conduit. The valves were then removed from the dissecting solution (ultrapure water containing 50 mM Tris-HCl (pH 7.2), 5 mM EDTA, and one or more antibiotics) and transferred to the deformable (plastic) processing vessel (FIG. 2). Prior to closing the processing vessel, a portion of the first processing (extracting) solution was gently added to the processing vessel and the side access port closed using the clamping mechanism illustrated in FIG. 2. The proximal end of the heart valve(s) was placed towards the inlet port and the distal end(s) of the valve was placed towards the outlet port. At this point, the processing vessel was placed such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 350 mm. Finally, sterile disposable tubing was attached between the top (outlet) port of the processing vessel and the solution reservoir. Sterile, in-line, filters were added at appropriate positions in the fluid flow to safeguard sterility during processing. The first processing (extracting) solution was pumped into, through and out of the processing vessel such that flow of fluids through the luminal part of the heart valve tubule passed into the processing vessel to affect constant solution change in the processing vessel and out through the outlet port to a solution reservoir. By processing the heart valve in a noninverted state, air which had been "trapped" in the luminal spaces behind the leaflets of the heart valve was induced to exit facilitating equal access of the processing solutions to the heart valve tissue being processed. Processing of the valve and conduit tissue with the first processing (extracting) solution was performed at 25±5° C. for 16 hours using a flow rate of the first processing (extracting) solution of 50 mls/min. The first processing (extracting) solution consisted of 50 mM Tris-HCl (pH 7.2), 5 mM $MgCl_2$, 1% (w:v) Allowash Solution (as described in U.S. Pat. No. 5,556,379), and endonuclease (Benzonase, a registered product of EM Industries, Inc.) (41.8 Units/ml). Following processing with the first processing (extracting) solution, the first processing (extracting) solution was replaced with sterile ultrapure water (350 mls at a pump rate of 50 mls/min.) which was then replaced with an alkaline hypotonic solution containing about 1% by weight sodium dodecylsulfate (SDS) in ultrapure water buffered with 50 mM Tris-HCl (pH 7.2) (second processing (treating) solution). Under this processing procedure, only sufficient ultrapure water was circulated through the processing vessel to affect one volume change of solution in the processing vessel. Under the processing with second processing (treating) solution, this second solution was circulated (flow rate of 30 mls/min.) through the tissue at room temperature (25±5° C.), to avoid precipitation of the SDS at reduced temperatures, for a time period of 5 hours.

Following processing with the second processing solution, ultrapure sterile water was circulated through the tissue and processing vessel such that the available volume of washing solution approximated a 1000-fold dilution of the SDS present in the second processing solution with a flow rate of 1 ml/min. for 1.5 hours. Following washing in this final processing step, the heart valve(s) was (were) removed from the processing vessel and transferred into storage solution of 0.05% chlorine dioxide in sterile ultrapure water and packaged in a volume of this solution sufficient to cover the tissue.

EXAMPLE 5

Saphenous vein tissues (two) from each leg of an acceptable human donor were carefully dissected under sterile conditions to remove all visible fat deposits and side vessels were tied off using nonresorable suture materials such that the ties did not occur in close proximity to the long run of the vessel. Sutures can restrict the decellularization process and the tissues under the sutures were removed following decellularization. For long vein grafts (40-60 cm) (FIG. 1), the distal ends of the veins were cannulated onto the ribbed attachment of the inlet port(s) and single sutures used to secure each vein. Additional suture lines were attached to the proximal ends of the veins. The veins were then removed from the dissecting solution (ultrapure water containing 50 mM Tris-HCl (pH 7.2), 5 mM EDTA, and one or more antibiotics) and transferred to the processing vessel which had been temporarily inverted. The second suture line along with the vein was passed through the processing vessel and secured to a point on the outlet port end of the processing vessel. Prior to closing the processing vessel, a portion of the first processing (extracting) solution was gently added to the processing vessel and the inlet port, with attached vein, was then secured. At this point, the processing vessel was turned such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. The first processing (extracting) solution was pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the first processing (extracting) solution was performed at 25±5° C. for 18 hours using a flow rate of the first processing (extracting) solution of 30 mls/min. The first processing (extracting) solution consisted of 50 mM Tris-HCl (pH 7.2), 5 mM $MgCl_2$, 1% (w:v) Allowash Solution (as described in U.S. Pat. No. 5,556,379), and endonuclease (Benzonase, a registered product of EM Industries, Inc.) (41.8 Units/ml). Following processing with the first processing (extracting) solution, the first processing (extracting) solution was replaced with sterile ultrapure water (250 mls at a pump rate of 30 mls/min.) which was then replaced with an alkaline hypotonic solution containing about 1% by weight sodium dodecylsulfate (SDS) in ultrapure water buffered with 50 mM Tris-HCl (pH 7.2) (second processing (treating) solution). Under this processing procedure, only sufficient ultrapure water was circulated through the processing vessel to affect one volume change of solution in the processing vessel. Under the processing with second processing solution, this second solution was circulated (flow rate of 30 mls/min.) through the tissue at room temperature (25±5° C), to avoid precipitation of the SDS at reduced temperatures, for a time period of than 1.5 hours. Following processing with the second processing solution, ultrapure sterile water was circulated through the tissue and processing vessel such that the available volume of washing solution approximated a 1000-fold dilution of the SDS present in the second processing (treating) solution with a flow rate of 1 ml/min. for 6 hours. Following washing in this final processing step, the vein was removed from the processing vessel and transferred into storage solution of isotonic saline in sterile ultrapure water and packaged in a volume of this solution sufficient to cover the tissue. The packaged tissue was gamma-radiation sterilized at 2.5 Mrads and stored at room temperature until use.

EXAMPLE 6

Saphenous vein tissues (two) from each leg of an acceptable human donor were carefully dissected under sterile conditions to remove all visible fat deposits and side vessels tied off using nonresorable suture materials such that the ties did not occur in close proximity to the long run of the vessel. Sutures can restrict the decellularization process and the tissues under the sutures will be removed following decellularization. For long vein grafts (40-60 cm) (FIG. 1), the distal ends of the veins were cannulated onto the ribbed attachment of the inlet port(s) and single sutures used to secure each vein. Additional suture lines were attached to the proximal ends of the veins. At this point, the veins were removed from the dissecting solution (ultrapure water containing 50 mM Tris-HCl (pH 7.2), 5 mM EDTA, and antibiotic solution for cardiovascular tissue procurement and transport) and transferred to the processing vessel(s) which had been temporarily inverted. The second suture line along with the vein was passed through the processing vessel and secured to a point on the outlet port end of the processing vessel. Prior to closing the processing vessel, a portion of the First Processing Solution was gently added to the processing vessel and the inlet port, with attached vein, was then secured. At this point, the processing vessel was turned such that the inlet port was down and the outlet port was up and the vessel attached to its support racking system via clamps, respectively. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 250 ml. Finally, sterile disposable tubing was attached between the top (outlet) port of the processing vessel and the solution reservoir. Sterile, in-line, filters were added at appropriate positions in the fluid flow to safeguard sterility during processing. First Processing Solution was pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the First Processing Solution was performed at temperatures approximating 25±5° C. for 16 hours using a flow rate of the First Processing Solution of 50 mls/min. The First Processing Solution consisted of 50 mM Tris-HCl (pH 8), 2 mM $MgCl_2$, 1% (w:v) Allowash Solution (as described in U.S. Pat. No. 5,556,379), and endonuclease (Benzonase, a registered product of EM Industries, Inc.) (41.8 Units/1 ml). Following processing with the First Processing Solution, the First Processing Solution was replaced with sterile ultrapure water containing 0.5 M NaCl (250 mls at a pump rate of 50 mls/min.) over a period of 1 hour, which was then replaced with an alkaline hypotonic solution containing about 0.001% by weight sodium dodecylsulfate (SDS) in ultrapure water buffered with 50 mM Tris-HCl (pH 9) (Second Processing Solution). Under this processing procedure, only sufficient ultrapure water salt solution needed to be circulated through the processing vessel to affect one volume change of solution in the processing vessel. Under the processing with Second Processing Solution, this second solution was circulated (flow rate of 50 mls/min.) through the tissue at room temperature (25±5° C.), to allow precipitation of the SDS at reduced temperatures, for a time period of than 3 hours. Following processing with the Second Processing Solution, ultrapure sterile water containing 0.01 M calcium chloride was circulated through the tissue and processing vessel such that the available volume of washing solution approximated a 1000-fold dilution of the SDS present in the Second Processing Solution with a flow rate of 50 ml/min. for 1.5 hours. Following washing in this final processing step, the vein was removed from the processing vessel and transferred into storage solution of 0.001% chlorine dioxide in sterile ultrapure water and packaged in a volume of this solution sufficient to cover the tissue.

EXAMPLE 7

Saphenous vein tissues (two) from each leg of an acceptable human donor were carefully dissected under sterile conditions to remove all visible fat deposits and side vessels tied off using nonriesorbable suture materials such that the ties did not occur in close proximity to the long run of the vessel. Sutures can restrict the decellularization process and the tissues under the sutures will be removed following decellularization. For these long vein grafts (33 and 28 cm) (FIG. 1), the distal ends of the veins were cannulated onto the ribbed attachment of the inlet port(s) and single sutures used to secure each vein. Additional suture lines were attached to the proximal ends of the veins. At this point, the veins were removed from the dissecting solution (ultrapure water and antibiotic solution including: 100 mcg/ml polymyxin B sulfate, 240 mcg/ml cefoxitin, 50 mcg/ml vancomycin, 120 mcg/ml lincomycin HCL, (for use with heart valves and arteries, when veins are processed, 0.12 mg/ml papaverive is added) in RMI 1640 tissue culture media, and transferred to the processing vessel(s) which had been temporarily inverted. The second suture line along with the vein was passed through the processing vessel and secured to a point on the outlet port end of the processing vessel. Prior to closing the processing vessel, a portion of the First Processing Solution was gently added to the processing vessel and the inlet port, with attached vein, was then secured. At this point, the processing vessel was turned such that the inlet port was down and the outlet port was up and the vessel attached to its support racking system via clamps, respectively. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 250 ml. Finally, sterile disposable tubing was attached between the top (outlet) port of the processing vessel and the solution reservoir. Sterile, in-line, filters were optionally added at appropriate positions in the fluid flow to safeguard sterility during processing. First Processing Solution was pumped into, through and out of the processing vessel such that flow of fluids through the luminal part of the vein tubule passed into the processing vessel to affect constant solution change in the processing vessel and out through the outlet port to a solution reservoir. By processing the vein in an inverted state, air which had been "trapped" in the luminal space of the vein was induced to exit facilitating equal access of the processing solutions to the vein tissue being processed. Processing of the vein tissue with the First Processing Solution was performed at temperatures ranging between 25±5° C. for 16 hours using a flow rate of the First Processing Solution of 50 mls/minute. The First Processing Solution consisted of 50 mM Tris-HCl (pH 8), 2 mM $MgCl_2$, 1% (w:v) Triton X-100, and endonuclease (Benzonase, a registered product of EM Industries, Inc.) (41.8 Units/ml). Following processing with the First Processing Solution, the First Processing Solution was replaced with a sterile water solution of 1.0 M KCl (50 mls/min. flow rate over 1.5 hours) and then by an alkaline hypotonic solution containing about 1% by weight sodium dodecylsulfate (SDS) in ultrapure water buffered with 50 mM Tris-HCl (pH 9) (Second Processing Solution). Under the processing with Second Processing Solution, this second solution was circulated (flow rate of 50 mls/min.) through the tissue at room temperature (25±5° C.), to allow deposition/precipitation of the SDS at reduced temperatures, for a time period of 3 hours. Following processing with the Second Processing Solution, ultrapure sterile water was circulated through the tissue and processing vessel such that the available volume of washing solution approximated a 1000-fold dilution of the SDS present in the Second Processing Solution with a flow rate of 50 ml/minute for 1.5 hours. Following washing in this final processing step, the vein was removed from the processing vessel and transferred into storage solution of 0.001% chlorine dioxide in sterile ultrapure water and packaged in a volume of this solution sufficient to cover the tissue.

EXAMPLE 8

Internal mammary artery tissues (two) from an acceptable human donor were carefully dissected under sterile conditions to remove all visible fat deposits and side vessels tied off using nonresorbable suture materials such that the ties did not occur in close proximity to the long run of the vessel. Sutures can restrict the decellularization process and the tissues under the sutures will be removed following decellularization. For short artery grafts (11 and 8 cm) (FIG. 1), one end of each artery were cannulated onto the ribbed attachment of the inlet port(s) and single sutures used to secure each arteries. At this point, the arteries were removed from the dissecting solution (ultrapure water containing 50 mM Tris-HCl (pH 7.2), 5 mM EDTA, and antibiotic solution for cardiovascular tissue procurement and transport) and transferred to the processing vessel(s) which had been temporarily inverted. Prior to closing the processing vessel, a portion of the First Processing Solution was gently added to the processing vessel and the inlet port, with attached artery, was then secured. At this point, the processing vessel was turned such that the inlet port was down and the outlet port was up and the vessel attached to its support racking system via clamps, respectively. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 150 ml. Finally, sterile disposable tubing was attached between the top (outlet) port of the processing vessel and the solution reservoir. Sterile, in-line, filters were added at appropriate positions in the fluid flow to safeguard sterility during processing. First Processing Solution was pumped into, through and out of the processing vessel such that flow of fluids through the luminal part of the artery tubule passed into the processing vessel to affect constant solution change in the processing vessel and out through the outlet port to a solution reservoir. By processing the artery in an inverted state, air which had been "trapped" in the luminal space of the vein was induced to exit facilitating equal access of the processing solutions to the vein tissue being processed. Processing of the artery tissue with the First Processing Solution was performed at temperatures approximating 25±5° C. for 16 hours using a flow rate of the First Processing Solution of 50 mls/hour. The First Processing Solution consisted of 50 mM Tris-HCl (pH 7.2), 5 mM $MgCl_2$, 1% (w:v) Allowash Solution (as described in U.S. Pat. No. 5,556,379), and endonuclease (Benzonase, a registered product of EM Industries, Inc.) (41.8 Units/ml). Following processing with the First Processing Solution, the First Processing Solution was replaced with sterile ultrapure water amended with 0.5 M $CaCl_2$ (250 mls at a pump rate of 60 mls/minute) which was then replaced with an alkaline hypotonic solution containing about 0.001% by weight sodium dodecylsulfate (SDS) in ultrapure water buffered with 50 mM Tris-HCl (pH 8) (Second Processing Solution). Under this processing procedure, only sufficient ultrapure salt solution needed to be circulated through the processing vessel to affect one volume change of solution in the processing vessel. Under the processing with Second Processing Solution, this second solution was circulated (flow rate of 30 mls/min.) through the tissue at room temperature (25±5° C), to allow precipitation of the SDS at reduced temperatures, for a time period of 3 hours. Following processing with the Second Processing Solution, ultrapure sterile water was circulated through the tissue and processing vessel such that the available volume of washing solution approximated a 1000-fold dilution of the SDS present in the Second Processing Solution with a flow rate of 50 l/min. for 1.5 hours. Following washing in this final processing step, the artery was removed from the processing vessel and transferred into storage solution of 70% (v:v) pharmaceutical grade isopropanol in sterile ultrapure water and packaged in a volume of this solution sufficient to cover the tissue.

EXAMPLE 9

Aortic and pulmonary tissues (one each) from a heart of an acceptable human donor were carefully dissected under sterile conditions to remove all visible fat deposits and cardiac muscle tissue (leaving only a small but visible band of cardiac muscle tissue around the proximal end of the conduit. At this point, the valves were removed from the dissecting solution (ultrapure water and antibiotic solution for cardiovascular tissue procurement and transport) and transferred to the deformable (plastic) processing vessel(s). Prior to closing the processing vessel, a portion of the First Processing Solution was gently added to the processing vessel and the side access port closed using the clamping mechanism illustrated in FIG. 2. The proximal end of the heart valve(s) was placed towards the inlet port and the distal end(s) of the valve was placed towards the outlet port. At this point, the processing vessel was placed such that the inlet port was down and the outlet port was up and the vessel attached to its support racking system via clamps. Sterile disposable tubing was attached to the inlet port and to pump tubing in a peristaltic pump. Further, sterile disposable tubing was attached to the inflow side of the peristaltic pump and to the solution reservoir which contained all remaining first processing solution. Total processing solution volume approximated 350 ml. Finally, sterile disposable tubing was attached between the top (outlet) port of the processing vessel and the solution reservoir. Sterile, in-line, filters were added at appropriate positions in the fluid flow to safeguard sterility during processing. First Processing Solution was pumped into, through and out of the processing vessel such that flow of fluids through the luminal part of the heart valve tubule passed into the processing vessel to affect constant solution change in the processing vessel and out through the outlet port to a solution reservoir. By processing the heart valve in an noninverted state, air which had been "trapped" in the luminal spaces behind the leaflets of the heart valve was induced to exit facilitating equal access of the processing solutions to the heart valve tissue being processed. Processing of the valve and conduit tissue with the First Processing Solution was performed at temperatures approximating 25±5° C. for 16 hours using a flow rate of the First Processing Solution of 50 mls/minute. The First Processing Solution consisted of 50 mM Tris-HCl (pH 8), 2 mM $MgCl_2$, 1% (w:v) Allowash Solution (as described in U.S. Pat. No. 5,556,379), and endonuclease (Benzonase, a registered product of EM Industries, Inc.) (83 Units/ml). Following processing with the First Processing Solution, the First Processing Solution was replaced with sterile ultrapure water (350 mls at a pump rate of 50 mls/min. being recirculated over a period of 3 hours) which was then replaced with an alkaline hypertonic solution containing about 024% by weight sodium dodecylsulfate (SDS) in ultrapure water buffered with 50 mM Tris-HCl (pH 7.2) containing 0.5 M sodium chloride (Second Processing Solution). This specific formulation of SDS and sodium chloride is balanced so as not to precipitate the SDS, the SDS concentration is minimized to lessen extension of the tissue dimensions, the salt concentration is maximized so as to facilitate limited contraction of the tissue dimensions-yet not be so concentrated as to precipitate the anionic detergent, and the whole processing solution facilitates decellularization and treatment of the tissue yet promotes coaptation of the valve leaflets post decellularization. Second Processing Solution was replaced with a hypertonic solution of 0.005 M calcium hydroxide. Under this processing procedure, only sufficient ultrapure water salt solution needed to be circulated through the processing vessel to affect one volume change of solution in the processing vessel. Under the processing with Second Processing Solution, this second solution was circulated (flow rate of 30 mls/minute) through the tissue at room temperature (25±5° C.), to allow precipitation of the SDS at reduced temperatures, for a time period of 5 hours. Following processing with the Second Processing Solution, ultrapure sterile water containing calcium ion was circulated through the tissue and processing vessel such that the available volume of washing/treatment solution approximated a 1000-fold dilution of the SDS present in the Second Processing Solution with a flow rate of 50 ml/min. for 1.5 hours. Following washing in this final processing step, the heart valve(s) was (were) removed from the processing vessel and transferred into storage solution of 0.05% chlorine dioxide in sterile ultrapure water and packaged in a volume of this solution sufficient to cover the tissue.

While the invention has been described in connection with specific embodiments thereof, it will be understood that it is capable of further modifications and this application is intended to cover any variations, uses, or adaptations of the invention following, in general, the principles of the invention and including such departures from the present disclosure as come hypotonic buffered within known or customary practice within the art to which the invention pertains and as may be applied to the essential features hereinbefore set forth as follows in the scope of the appended claims. Any references including patents cited herein are incorporated herein in their entirety.1.

What is claimed is:

1. A process for preparing commercializable quantities of acellular soft tissue grafts for implantation into mammalian systems, comprising:
   obtaining tissue samples from an acceptable donor;
   extracting said tissue samples with a hypotonic extracting solution comprising one or more nonionic detergents and one or more endonucleases, to produce extracted tissue;
   treating said extracted tissue with a treating solution comprising one or more anionic detergents, to produce a treated tissue, wherein the treating solution has 0.001% to 0.024% (w:v) of the one or more anionic detergents;
   washing said treated tissue with a decontaminating solution comprising one or more decontaminating agents; to produce said acellular soft tissue graft; and
   storing said acellular soft tissue graft in a storage solution comprising one or more decontaminating agents.

2. The process of claim 1, said one or more decontaminating agents comprise one or more antimicrobial agents.

3. The process of claim 1, said hypotonic extracting solution having an alkaline pH.

4. The process of claim 1, said hypotonic extracting solution further comprises one or more organic or inorganic buffers, wherein an alkaline pH is maintained, and an osmolality of the hypotonic extracting solution which is hypotonic to the cells in said soft tissue is maintained.

5. The process of claim 1, wherein said nonionic detergent comprise one or more detergents selected from the group consisting of: polyxyethylene alcohol, polyoxyethylene isoalcohol, polyoxyethylene p-t-octylphenol, polyoxyethylene nonylphenol, polyoxyethylene esters of fatty acids, and polyoxyethylene sorbitol esters.

6. The process of claim 1, said treating solution comprises one or more buffers selected from the group consisting of: an organic buffer and an inorganic buffer, wherein an alkaline pH is maintained, and an osmolality of the treating solution which is hypotonic to the cells in said soft tissue is maintained.

7. The process of claim 1, said one or more anionic detergents are selected from the group consisting of: sodium dodecysulphate, sodium dodecylsulphonate, sodium dodecyl-N-sarcosinate, and sodium suramin.

8. The process of claim 1, said decontaminating solution comprises ultrapure, endotoxin-free, water solutions of antimicrobial agents, wherein said antimicrobial agents are non-reactive towards said one or more anionic detergents.

9. The process of claim 1, said storage solution comprises ultrapure, endotoxin-free, water.

10. The process of claim 9, wherein said storage solution further comprises one or more antimicrobial agents.

11. The process of claim 10, wherein said one or more antimicrobial agents comprise one or more members selected from the group consisting of: chlorine dioxide, ethanol, isopropanol, methanol, glycerol, and methylparaben.

12. The process of claim 11 wherein said chlorine dioxide or said methylparaben are present in said storage solution at a concentration in the range of from 0.001% to 0.1% (v:v).

13. The process of claim 11, wherein said ethanol, isopropanol, methanol, or glycerol are present in said storage solution at a concentration in the range of from 60% to 90% (v:v).

14. The process of claim 1, said one or more endonucleases comprise one or more broad spectrum endonucleases capable of degrading both deoxyribonucleic acids and ribonucleic acids.

15. The process of claim 14, wherein said one or more broad-spectrum endonucleases comprise one or more recombinant endonucleases.

16. The process of claim 15, wherein said one or more recombinant endonucleases comprise Benzonase®.

17. The process of claim 14, said one or more endonucleases are present in said hypotonic extracting solution at a concentration sufficient to degrade nucleic acids present in said tissue sample.

18. The process of claim 17, wherein said one or more endonucleases are present in said hypotonic extracting solution at a concentration of from about 30 IU/ml tissue to about 70 IU/ml tissue.

* * * * *